(12) United States Patent
Kobayashi et al.

(10) Patent No.: US 7,741,242 B2
(45) Date of Patent: Jun. 22, 2010

(54) PALLADIUM CATALYST COMPOSITION

(75) Inventors: Shu Kobayashi, Tokyo (JP); Atsunori Sano, Tokyo (JP); Keiji Oono, Kawagoe (JP)

(73) Assignees: Wako Pure Chemical Industries, Ltd., Osaka (JP); Japan Science and Technology Corporation, Kawaguchi-Shi (JP)

( * ) Notice: Subject to any disclaimer, the term of this patent is extended or adjusted under 35 U.S.C. 154(b) by 0 days.

(21) Appl. No.: 10/527,699

(22) PCT Filed: Sep. 1, 2003

(86) PCT No.: PCT/JP03/11131

§ 371 (c)(1),
(2), (4) Date: Mar. 11, 2005

(87) PCT Pub. No.: WO2004/024323

PCT Pub. Date: Mar. 25, 2004

(65) Prior Publication Data

US 2006/0019822 A1    Jan. 26, 2006

(30) Foreign Application Priority Data

Sep. 13, 2002  (JP) ............................. 2002-267798

(51) Int. Cl.
B01J 23/44    (2006.01)
B01J 37/00    (2006.01)

(52) U.S. Cl. ................. 502/339; 502/173; 526/273; 526/320; 526/326; 526/318.1; 526/328; 526/322

(58) Field of Classification Search ............ 502/159, 502/103, 326, 169.1, 333, 213, 339, 173; 568/471, 579; 526/904
See application file for complete search history.

(56) References Cited

U.S. PATENT DOCUMENTS

| | | | | |
|---|---|---|---|---|
| 4,258,206 A * | 3/1981 | Pittman et al. | ............. | 560/233 |
| 4,548,963 A * | 10/1985 | Cluff et al. | ............. | 523/427 |
| 4,943,482 A * | 7/1990 | Charmot et al. | ............. | 428/407 |
| 5,045,436 A * | 9/1991 | Tieke et al. | ............. | 430/315 |
| 5,770,755 A * | 6/1998 | Schertl et al. | ............. | 556/43 |
| 6,054,507 A * | 4/2000 | Funaki et al. | ............. | 523/210 |
| 6,452,043 B1 * | 9/2002 | Zoeller et al. | ............. | 560/232 |
| 6,627,770 B1 * | 9/2003 | Cheung et al. | ............. | 562/519 |
| 6,716,792 B2 * | 4/2004 | Okamoto et al. | ............. | 502/402 |
| 6,743,873 B2 * | 6/2004 | Kirk et al. | ............. | 526/204 |
| 6,916,954 B2 * | 7/2005 | Schafer et al. | ............. | 562/517 |
| 2002/0045708 A1 * | 4/2002 | Okamoto et al. | ............. | 525/107 |

FOREIGN PATENT DOCUMENTS

| | | | |
|---|---|---|---|
| JP | 59-27840 | | 2/1984 |
| JP | 5-212291 | | 8/1993 |
| JP | 8-325204 | | 12/1996 |
| JP | 2002-253972 | * | 9/2002 |
| JP | 2002-275116 | * | 9/2002 |

OTHER PUBLICATIONS

Akiyama, R.; Kobayashi, S. J. Am. Chem. Soc., 2003, 125, 3412-3413.*
An et al. Polymers for Advanced Technologies, 1996, 7, 652-656.*
Kluytmans et al. Catalysis Today, 2000, 57, 143-155.*
XP-002340174; Toshima et al; "Substrate Selectivity by the Polymer Support in Hydrogenation Over Crosslinked Polymer-Immobilized Metal Catalysts;" Reactive Polymers, 15 (1991) pp. 135-145.
XP-002340175; Kralik et al; "Microporous poly-N,N-dimethylacrylamide-p-styrylsulfonate-methylene bis(acrylamide): a promising support for metal catalysis;" J. Molecular Catalysis A: Chemical; 97 (1995) pp. 145-155.
XP-002340176; Corain et al; "Generating palladium nanoclusters inside functional cross-linked polymer frameworks;" J. Molecular Catalysis A: Chemical; 173 (2001) pp. 99-115.
European Search Report dated Aug. 25, 2005.

* cited by examiner

*Primary Examiner*—David Wu
*Assistant Examiner*—Rip A. Lee
(74) *Attorney, Agent, or Firm*—Kratz, Quintos & Hanson, LLP

(57) ABSTRACT

The present invention discloses 1) a catalyst composition consisting of a crosslinked organic polymer compound and a palladium catalyst, wherein said catalyst is physically carried on said crosslinked organic polymer compound, 2) a manufacturing method of the above catalyst composition 1), characterized by homogenizing a straight chain organic polymer compound, having a crosslinkable functional group, and a palladium catalyst in a solvent dissolving said straight chain organic polymer compound, then depositing a composition thus formed and subjecting the crosslinkable functional group in said deposit to a crosslinking reaction, 3) a method for substitution reaction at an allyl position, characterized by reacting an allyl carbonate and a neucleophilic agent in the presence of the above catalyst composition 1), and 4) a method for oxidizing an alcohol, characterized by subjecting the above catalyst composition 1) to reaction with an alcohol.

10 Claims, No Drawings

PALLADIUM CATALYST COMPOSITION

TECHNICAL FIELD

The present invention relates to a catalyst composition comprising a palladium catalyst carried on a crosslinked organic polymer compound, which has superior solvent resistance and keeps activity thereof in repeated use.

BACKGROUND OF THE INVENTION

Palladium is known as a useful catalyst since it induces various conversion reactions in organic synthesis. However, this metal has many problems in direct use as a catalyst because it is expensive and in addition, it loses partially its activity on contact with air and cannot be used repeatedly. Fixation of palladium on a polymer as a technology to solve these problems has been attempted and various reactions using palladium fixed on a polymer have been reported frequently so far. However, any of conventional palladium fixed on a polymer still has a common problem that catalyst recovery rate is low and activity decreases in repeated use, although stability of the catalyst itself is improved.

For example, the present inventors created a microcapsulated metal catalyst by fixing a palladium compound such as a palladium complex compound, an organic palladium compound, an inorganic salt and an organic salt, on a polystyrene-type compound, a polymer compound having an aromatic ring (for example, see the specification of Japanese application; JP-2001-59742). However, the above microcapsulated metal catalyst turned out to be difficult to use for a reaction employing a general organic solvent, because any of polymer compounds used as carriers is a non-crosslinked type and has defect of easily dissolving in an organic solvent to be used for a common organic reaction, such as methylene chloride, tetrahydrofuran, benzene and toluene. Because the polymer compound to be used as a carrier of the above microcapsulated metal catalyst was a non-crosslinked type, said metal-catalyst composition agglomerated easily, resulting in smaller surface area of said metal-catalyst composition, which caused a problem of very low catalyst efficiency due to smaller amount of actually functioning catalyst compared with an amount of the metal carried on a polymer carrier. Another problem was that raw materials or reaction products were caught into a carrier polymer constituting a catalyst composition in a reaction using these metal catalysts.

To solve these problems, the present inventors studied use of a crosslinked polymer carrier obtained by crosslinking with divinylbenzene or the like, as the above polystyrene-type polymer compound. However, it turned out to be impossible to fix a metal on polystyrene crosslinked by divinylbenzene, which is insoluble in a general organic solvent, because it was necessary to dissolve a polymer carrier in a solvent in order for the polymer to carry the metal physically.

On the other hand, a method for fixing a metal catalyst on a crosslinked polymer to which an ion-exchange group is introduced has been known as a method for fixing a metal catalyst on such a crosslinked polymer carrier (see Jp-A-59-27840, for example). However, a metal catalyst carried on a carrier obtained by such a method was sometimes difficult to use repeatedly due to leakage of the carried metal catalyst depending on properties of liquid to be used with.

In such situations, a more versatile new metal catalyst carried on a crosslinked polymer wherein the polymer carrier is insoluble in an organic solvent and the carried metal hardly leaks and can keep its activity in repeated use has been required.

SUMMARY OF THE INVENTION

The present invention provides 1) a catalyst composition comprising a crosslinked organic polymer compound and a palladium catalyst, wherein said catalyst is physically carried on said crosslinked organic polymer compound, 2) a manufacturing method of the above catalyst composition 1), characterized by homogenizing a straight chain organic polymer compound having a crosslinkable functional group and a palladium catalyst in a solvent dissolving said straight chain organic polymer compound, then depositing a composition thus formed and subjecting the crosslinkable functional group in said deposit composition to a crosslinking reaction, 3) a method for substitution reaction at an allyl position, characterized by reacting an allyl carbonate and a neucleophilic agent in the presence of the above catalyst composition 1), and 4) a method for oxidizing an alcohol, characterized by subjecting the above catalyst composition 1) to reaction with an alcohol.

That is, the present inventors have found, after intensive study to attain the above objectives, that by homogenizing a straight chain organic polymer compound having a crosslinkable functional group and a palladium catalyst in a solvent dissolving said straight chain organic polymer compound, then depositing a composition formed and subjecting the crosslinkable functional group in said deposit composition to a crosslinking reaction, a catalyst composition can easily be prepared, which comprising a crosslinked organic polymer compound and a palladium catalyst, wherein said catalyst is physically carried on said crosslinked organic polymer compound. The inventors have further found that thus obtained catalyst composition has higher activity than conventional palladium catalysts in various reactions and superior solvent resistance, leading to durable activity even in repeated use, as well as is easily handled, and thus the present invention has been completed. In addition, after further intensive study, the present inventors have found that by homogenizing a straight chain organic polymer compound of particular structure having a crosslinkable functional group and Pd(0) coordinated by a ligand, in a solvent dissolving said straight chain organic polymer compound, then depositing a composition formed and subjecting the crosslinkable functional group in said deposit composition to a crosslinking reaction, a catalyst composition where Pd(0) not coordinated by a ligand is physically carried can also be synthesized easily, and thus the present invention has been completed.

BEST MODE FOR CARRYING OUT OF THE INVENTION

A palladium catalyst relating to the present invention includes any compound as long as it can be used as a palladium catalyst in this field, and a compound derived from Pd(0), Pd(I) and Pd(II) is preferable. A compound derived from Pd(0) includes Pd(0) itself (having no ligand, etc.) and a Pd(0) complex coordinated by a ligand. A compound derived from Pd(I) includes dichloro-µ-bis[bis(dimethylphosphino)methane]dipalladium ($Pd_2Cl_2[(CH_3)_2PCH_2P(CH_3)_2]_2$), dichloro-µ-bis[bis(diphenylphosphino)methane]dipalladium ($Pd_2Cl_2[Ph_2PCH_2PPh_2]_2$), etc., and a compound derived from Pd(II) includes, for example, a Pd(II) salt such as halogenated Pd(II) (chloride, bromide, iodide, etc.), Pd(II) carboxylates, (acetate, propionate). Among these, Pd(0) and a Pd(II) salt are preferable and Pd(0) is more preferable.

A ligand of a Pd(0) complex includes 1,5-cyclooctadiene (COD), dibenzylideneacetone (DBA), bipyridine (BPY), phenanthroline (PHE), benzonitrile (PhCN), isocyanide (RNC), triethylarsine (As(Et$_3$)), organic phosphine ligands such as dimethylphenylphosphine (P(CH$_3$)$_2$Ph), diphenylphosphinoferrocene (dPPf), trimethylphosphine (P(CH$_3$)$_3$), triethylphosphine (P(Et)$_3$), tri-tert-butylphosphine (P($^t$-Bu)$_3$), tricyclohexylphosphine (PCy$_3$), trimethoxyphosphine (P(OCH$_3$)$_3$), triethoxyphosphine (P(OEt)$_3$), tri-tert-butoxyphosphine (P(O$^t$-Bu)$_3$), triphenylphosphine (PPh$_3$), 1,2-bis(diphenylphosphino) ethane (DPPE), triphenoxyphosphine (P(OPh)$_3$), etc. Among these, an organic phosphine ligand, particularly triphenylphosphine, tri-tert-butylphosphine, triethylphosphine, trimethylphosphine, and the like are preferable. Among these, triphenylphosphine is more preferable. When a palladium catalyst carried on a catalyst composition of the present invention is Pd(0) having ligands, the number of the ligands is usually 1 to 4, depending on kinds of straight chain organic polymer compounds used in preparation, crosslinking reaction conditions, etc.

A crosslinked organic polymer compound includes, for example, a crosslinked compound of a polymer or a copolymer obtained by polymerizing or copolymerizing one or more kinds of 1) monomers having a crosslinkable functional group and a polymerizable double bond, and a crosslinked compound of a copolymer obtained by copolymerizing one or more kinds of 1) monomers having a crosslinkable functional group and a polymerizable double bond and one or more kinds of 2) monomers having a polymerizable double bond. Among these compounds, a crosslinked compound of a copolymer obtained by copolymerizing two kinds of 1) monomers having a crosslinkable functional group and a polymerizable double bond and one kind of 2) monomer having a polymerizable double bond is preferable.

A crosslinkable functional group includes, for example, a condensable group by a condensation reaction such as dehydration condensation by adding an acid or heating and a reactable group with a suitable crosslinking agent, and specifically includes an epoxy group, a carboxyl group, a hydroxyl group, an acyloxy group, an isocyanate group, an amino group, etc.

A monomer unit constituting a copolymer before crosslinking the above crosslinked organic polymer compound is a monomer unit derived from a monomer having a crosslinkable functional group and a polymerizable double bond, or a monomer unit derived from a monomer having a polymerizable double bond.

Ratio of a monomer unit derived from a monomer having a crosslinkable functional group and a polymerizable double bond, to the whole copolymer before crosslinking, in a crosslinked organic polymer compound relating to the present invention, is usually 0.1 to 100% by mol, preferably 1 to 50% by mol, more preferably 5 to 40% by mol and still more preferably 5 to 20% by mol.

A polymer or a copolymer before crosslinking a crosslinked organic polymer compound relating to the present invention is a so-called straight chain organic polymer compound. A monomer having a crosslinkable functional group and a polymerizable double bond, which is a raw material of the above straight chain organic polymer compound, includes, for example, (1) a glycidyl compound having an epoxy group as a crosslinkable functional group, selected from a glycidyl ether or a glycidyl ester represented by the following general formula [1] or [2], respectively:

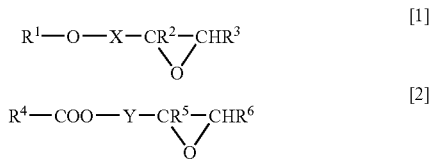

(wherein R$^2$, R$^3$, R$^5$ and R$^6$ each independently represents a hydrogen atom or an alkyl group having 1 to 6 carbon atoms; X and Y each independently represents an alkylene group having 1 to 6 carbon atoms; R$^2$ may form a ring of 3 to 6 members together with carbon atoms of R$^3$ or X, and R$^5$ may form a ring of 3 to 6 members together with carbon atoms of R$^6$ or Y; and R$^1$ and R$^4$ each independently is a group represented by the following general formula [3]:

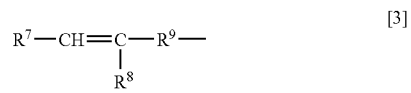

[wherein R$^7$ and R$^8$ each independently represents a hydrogen atom or an alkyl group having 1 to 6 carbon atoms; R$^9$ represents a direct-linkage, an alkylene group having 1 to 6 carbon atoms, an arylene group having 6 to 9 carbon atoms, an arylalkylene group having 7 to 12 carbon atoms or an arylenealkylene group having 7 to 15 carbon atoms; and an aromatic ring in the above aryl group or aralkyl group may have an alkyl group having 1 to 4 carbon atoms, an alkoxy group having 1 to 4 carbon atoms and/or a halogen atom, as a substituent]), (2) a monomer having a carboxyl group as a crosslinkable functional group, represented by the following general formula [4]:

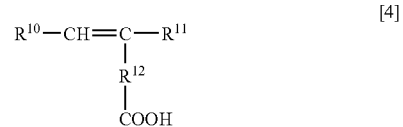

(wherein R$^{10}$ represents a hydrogen atom or an alkyl group having 1 to 6 carbon atoms; R$^{11}$ represents a hydrogen atom, an alkyl group having 1 to 6 carbon atoms, an aryl group having 6 to 10 carbon atoms or an aralkyl group having 7 to 12 carbon atoms; and an aromatic ring in the above aryl group or aralkyl group may have an alkyl group having 1 to 4 carbon atoms, an alkoxy group having 1 to 4 carbon atoms and/or a halogen atom as a substituent; and R$^{12}$ represents a direct-linkage, an alkylene group having 1 to 6 carbon atoms, an arylene group having 6 to 9 carbon atoms, an arylalkylene group having 7 to 12 carbon atoms or an arylenealkylene group having 7 to 15 carbon atoms), or (3) a monomer having a hydroxyl group, an acyloxy group, an isocyanato group or an amino group as a crosslinkable functional group, represented by the following general formula [5]:

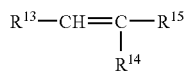    [5]

(wherein $R^{13}$ represents a hydrogen atom or an alkyl group having 1 to 20 carbon atoms; $R^{14}$ represents a hydroxyl group, an amino group, hydroxyalkyl group having 1 to 50 carbon atoms that may have a carbonyl group and/or an oxygen atom, a hydroxyaryl group having 6 to 10 carbon atoms, a hydroxyaralkyl group having 7 to 50 carbon atoms that may have a carbonyl group and/or an oxygen atom, a hydroxyalkylaryl group having 7 to 50 carbon atoms that may have a carbonyl group and/or an oxygen atom, an acyloxy group having 2 to 6 carbon atoms, an arylacyloxy group having 7 to 15 carbon atoms, an isocyanatoalkyl group having 2 to 7 carbon atoms, an isocyanatoaryl group having 7 to 20 carbon atoms, an isocyanatoaralkyl group having 8 to 20 carbon atoms, an isocyanatoalkylaryl group having 8 to 20 carbon atoms, an aminoalkyl group having 2 to 7 carbon atoms, an aminoaryl group having 7 to 20 carbon atoms, an aminoaralkyl group having 8 to 20 carbon atoms or an aminoalkylaryl group having 8 to 20 carbon atoms; an aromatic ring in the above hydroxyaryl group, hydroxyaralkyl group, hydroxyalkylaryl group, arylacyloxy group, isocyanatoaryl group, isocyanatoaralkyl group, isocyanatoalkylaryl group, aminoaryl group, aminoaralkyl group and aminoalkylaryl group may have an alkyl group having 1 to 4 carbon atoms, an alkoxy group having 1 to 4 carbon atoms and/or a halogen atom; $R^{15}$ represents a hydrogen atom, an alkyl group having 1 to 6 carbon atoms, an aryl group having 6 to 10 carbon atoms or an aralkyl group having 7 to 12 carbon atoms; and an aromatic ring in the above aryl group or aralkyl group may have an alkyl group having 1 to 4 carbon atoms, an alkoxy group having 1 to 4 carbon atoms and/or a halogen atom, as a substituent).

An alkyl group represented by $R^2$, $R^3$, $R^5$ and $R^6$ in a glycidyl ether or a glycidyl ester represented by the general formula [1] or [2], respectively, which is the above glycidyl compound (1) having an epoxy group and a polymerizable double bond, may be straight chain, branched or cyclic and includes a group having usually 1 to 6 carbon atoms, preferably 1 to 4 carbon atoms and more preferably 1 to 2 carbon atoms, and specifically a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a cyclopropyl group, a cyclopentyl group, a cyclohexyl group, etc.

Each of $R^2$ and $R^3$ in the general formula [1] is preferably a hydrogen atom, and each of $R^5$ and $R^6$ in the general formula [2] is preferably a hydrogen atom.

An alkylene group represented by X and Y may be straight chain, branched or cyclic and includes a group having usually 1 to 6 carbon atoms, preferably 1 to 4 carbon atoms and more preferably 1 to 2 carbon atoms, and specifically includes a methylene group, an ethylene group, a trimethylene group, a propylene group, a methylmethylene group, an methylethylene group, an ethylmethylene group, a tetramethylene group, a pentamethylene group, a hexamethylene group, a cyclopropylene group, a cyclopentylene group, a cyclohexylene group, etc.

An alkyl group represented by $R^7$ and $R^8$ in the general formula [3] may be straight chain, branched or cyclic and includes a group having usually 1 to 6 carbon atoms, preferably 1 to 4 carbon atoms and more preferably 1 to 2 carbon atoms, and specifically includes a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a cyclopropyl group, a cyclopentyl group, a cyclohexyl group, etc.

Each of $R^7$ and $R^8$ in the general formula [3] is preferably a hydrogen atom.

An alkylene group represented by $R^9$ may be straight chain, branched or cyclic and includes a group having usually 1 to 6 carbon atoms, preferably 1 to 4 carbon atoms and more preferably 1 to 2 carbon atoms, and specifically includes a methylene group, an ethylene group, a trimethylene group, a propylene group, a methylmethylene group, an methylethylene group, an ethylmethylene group, a tetramethylene group, a pentamethylene group, a hexamethylene group, a cyclopropylene group, a cyclopentylene group, a cyclohexylene group, etc.

An arylene group represented by $R^9$ includes usually a group having 6 to 9 carbon atoms and specifically includes a p-phenylene group, a o-phenylene group, a m-phenylene group, a 2-methylphenylene group, a 2,6-dimethylphenylene group, a 2,4-dimethylphenylene group, a 2,3-dimethylphenylene group, etc.

An arylalkylene group represented by $R^9$ includes usually a group having 7 to 12 carbon atoms and specifically includes a phenylmethylene group, a phenylethylene group, a 1-phenylpropylene group, a 2-phenylpropylene group, a 1-phenylbutylene group, a 2-phenylbutylene group, a naphthylmethylene group, a naphthylethylene group, etc.

An arylenealkylene group represented by $R^9$ includes a group having usually 7 to 15 carbon atoms and preferably 7 to 10 carbon atoms, and specifically, for example,

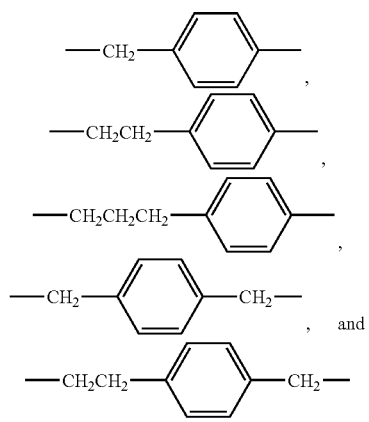

which are a combination of the above alkylene group and arylene group as appropriate.

$R^9$ represented by the general formula [3] is preferably an arylene group or an arylenealkylene group and particularly preferably an arylenealkylene group.

A ring that $R^2$ and $R^5$ each may form together with carbon atoms of $R^3$ or X, and carbon atoms of $R^6$ or Y, respectively in the general formulas [1] and [2] includes usually a ring of 3 to 6 members and specifically a cyclopropane ring, a cyclobutane ring, a cyclopentane ring, a cyclohexane ring, and the like.

A preferable glycidyl compound represented by the general formula [1] or [2] includes specifically glycidyl ethers such as vinylbenzyl glycidyl ether, vinylphenyl glycidyl ether, etc., glycidyl esters such as glycidyl benzoate, glycidyl phenylacetate, etc.

A particularly preferable glycidyl compound relating to the present invention is a glycidyl ethers represented by the general formula [1].

An alkyl group represented by $R^{10}$ and $R^{11}$ in the monomer represented by the general formula [4] having a carboxyl group and a polymerizable double bond in the above (2), may be straight chain, branched or cyclic and includes a group having usually 1 to 6 carbon atoms, preferably 1 to 4 carbon atoms and more preferably 1 to 2 carbon atoms, and specifically includes a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a cyclopropyl group, a cyclopentyl group, a cyclohexyl group, etc.

An aryl group represented by $R^{11}$ includes a group having usually 6 to 10 carbon atoms and preferably 6 carbon atoms, and specifically, for example, a phenyl group and a naphthyl group.

An aralkyl group represented by $R^{11}$ includes a group having usually 7 to 12 carbon atoms and preferably 7 to 10 carbon atoms, and specifically, a benzyl group, a phenylethyl group, a phenylpropyl group, a phenylbutyl group, a phenylpentyl group, a phenylhexyl group, etc.

An alkyl group which is used as a substituent that an aromatic ring in an aryl group and an aralkyl group represented by $R^{11}$ may have, may be straight chain or branched, and includes usually a group having 1 to 4 carbon atoms and specifically a methyl group, an ethyl group, an n-propyl group, an isopropyl group, an n-butyl group, an isobutyl group, a sec-butyl group, a tert-butyl group, etc., and an alkoxy group which is used as a substituent that the above aromatic ring may have, may be straight chain or branched, and includes usually a group having 1 to 4 carbon atoms, and specifically a methoxy group, an ethoxy group, a propoxy group, an isopropoxy group, a butoxy group, an isobutoxy group, a sec-butoxy group, a tert-butoxy group, etc. A halogen atom that the above aromatic ring may have, includes, for example, a chlorine atom, a fluorine atom, a bromine atom and an iodine atom.

The above substituents of usually 1 to 5 and preferably 1 to 2 may be present in an aromatic ring in an aryl group and aralkyl group, represented by $R^{11}$.

An alkylene group, arylene group, arylalkylene group and arylenealkylene group represented by $R^{12}$ in the general formula [4], include similar groups as those represented by the above $R^9$ in the general formula [3].

$R^{12}$ is preferably a direct-linkage in a monomer represented by the general formula [4] and such a monomer is also called an acrylic-acid-based monomer in the present invention.

Among acrylic-acid-based monomers, acrylic acid and methacrylic acid are more preferable examples, and methacrylic acid is particularly preferable.

An alkyl group represented by $R^{13}$ in the monomer represented by the general formula [5] having a hydroxyl group in the above (3), an acyloxy group, an isocyanato group or an amino group and a polymerizable double bond, may be straight chain, branched or cyclic and includes a group having usually 1 to 20 carbon atoms, preferably 1 to 10 carbon atoms, more preferably 1 to 6 carbon atoms, still more preferably 1 to 4 carbon atoms and particularly preferably 1 to 2 carbon atoms, and specifically includes a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a 3-methylpentyl group, a 2-methylpentyl group, a 1,2-dimethylbutyl group, an n-heptyl group, an isoheptyl group, a sec-heptyl group, an n-octyl group, an isooctyl group, a sec-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group, a cycloicosyl group, etc.

A hydroxyalkyl group represented by $R^{14}$ that may have a carbonyl group and/or an oxygen atom may be straight chain, branched or cyclic and includes a group having usually 1 to 50 carbon atoms, preferably 2 to 20 carbon atoms, more preferably 5 to 15 carbon atoms and still more preferably 8 to 13 carbon atoms, and specifically includes a hydroxymethyl group, a 1-hydroxyethyl group, a 2-hydroxyethyl group, a 1-hydroxy-n-propyl group, a 2-hydroxy-n-propyl group, a 3-hydroxy-n-propyl group, a 2-hydroxy-1-methylethyl group, a 1-hydroxy-1-methylethyl group, a 1-hydroxy-n-butyl group, a 2-hydroxy-n-butyl group, a 3-hydroxy-n-butyl group, a 4-hydroxy-n-butyl group, a 3-hydroxy-2-methylpropyl group, a 2-hydroxy-2-methylpropyl group, a 1-hydroxy-2-methylpropyl group, a 3-hydroxy-1-methylpropyl group, a 2-hydroxy-1-methylpropyl group, a 1-hydroxy-1-methylpropyl group, a 1-hydroxypentyl group, a 2-hydroxypentyl group, a 3-hydroxypentyl group, a 4-hydroxypentyl group, a 5-hydroxypentyl group, a 4-hydroxy-1-methylbutyl group, a 3-hydroxy-1-ethylpropyl group, a 1-hydroxy-1-ethylpropyl group, a 1-hydroxy-n-hexyl group, a 3-hydroxy-n-hexyl group, a 6-hydroxy-n-hexyl group, a 5-hydroxy-3-pentyl group, a 4-hydroxy-1,1-dimethylbutyl group, a 1-hydroxyheptyl group, a 7-hydroxyheptyl group, a 8-hydroxyoctyl group, a 9-hydroxynonyl group, a 10-hydroxydecyl group, a 11-hydroxyundecyl group, a 12-hydroxydodecyl group, a 13-hydroxytridecyl group, a 14-hydroxytetradecyl group, a 15-hydroxypentadecyl group, a 16-hydroxyhexadecyl group, a 17-hydroxyheptadecyl group, a 18-hydroxyoctadecyl group, a 19-hydroxynonadecyl group, a 20-hydroxyicosyl group, a 25-hydroxypentacosyl group, a 30-hydroxytriacontyl group, a 40-hydroxytetracontyl group, a 50-hydroxypentacontyl group, a 1-hydroxycyclopropyl group, a 2-hydroxycyclopropyl group, a 1-hydroxycyclopentyl group, a 2-hydroxycyclopentyl group, a 3-hydroxycyclopentyl group, a 1-hydroxycyclohexyl group, a 2-hydroxycyclohexyl group, a 3-hydroxycyclohexyl group, a 1-hydroxycycloheptyl group, a 2-hydroxycyclooctyl group, a 3-hydroxycyclononyl group, a 3-hydroxycyclodecyl group, a 4-hydroxycyclopentadecyl group, etc.

The above hydroxyalkyl group may have carbonyl groups of usually 1 to 5, preferably 1 to 2 and more preferably 1 in its chain or at the end of its chain, and/or oxygen atoms of usually 1 to 15, preferably 1 to 10 and more preferably 3 to 5 in its chain or at the end of its chain.

A hydroxyalkyl group represented by $R^{14}$ having a carbonyl group and/or an oxygen atom includes specifically, for example,

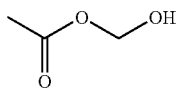 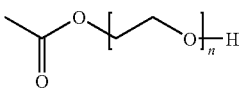

(wherein n is an integer of 1 to 6.)

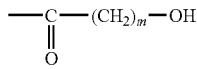

(wherein m is an integer of 1 to 15.)

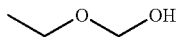 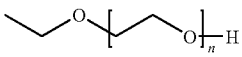

(wherein n is the same as the above.)

and among these, a hydroxyalkyl group having only oxygen atoms is preferable.

A hydroxyaryl group represented by $R^{14}$ includes a group having usually 6 to 10 carbon atoms and preferably 6 carbon atoms, and specifically, for example, a 2-hydroxyphenyl group, a 3-hydroxyphenyl group and a 4-hydroxyphenyl group.

A hydroxyaralkyl group represented by $R^{14}$ that may have a carbonyl group and/or an oxygen atom may be straight chain, branched or cyclic and includes a group having usually 7 to 50 carbon atoms, preferably 7 to 30 carbon atoms and more preferably 8 to 20 carbon atoms, and specifically includes a 2-hydroxyphenylmethyl group, a 3-hydroxyphenylmethyl group, a 4-hydroxyphenylmethyl group, a hydroxyphenylethyl group, a hydroxyphenylpropyl group, a hydroxyphenylbutyl group, a hydroxyphenylhexyl group, a hydroxyphenyheptyl group, a hydroxyphenyloctyl group, a hydroxyphenylnonyl group, a hydroxyphenyldecyl group, a hydroxyphenylundecyl group, a hydroxyphenyldodecyl group, a hydroxyphenyltridecyl group, a hydroxyphenyltetradecyl group, etc.

The above hydroxyaralkyl group may have carbonyl groups of usually 1 to 5, preferably 1 to 2 and more preferably 1 in its chain or at the end of its chain, and/or oxygen atoms of usually 1 to 15, preferably 1 to 10 and more preferably 3 to 5 in its chain or at the end of its chain.

A preferable hydroxyaralkyl group represented by $R^{14}$ having a carbonyl group and/or an oxygen atom includes specifically, for example,

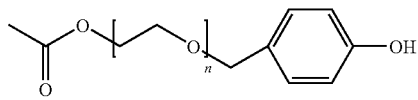

(wherein n is the same as the above.)

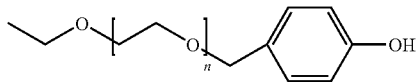

(wherein n is the same as the above.)

A hydroxyalkylaryl group represented by $R^{14}$ that may have a carbonyl group and/or an oxygen atom is straight chain, branched or cyclic and includes a group having usually 7 to 50 carbon atoms, preferably 7 to 30 carbon atoms and more preferably 8 to 20 carbon atoms, and specifically includes a 2-hydroxymethylphenyl group, a 3-hydroxymethylphenyl group, a 4-hydroxymethylphenyl group, a hydroxyethylphenyl group, a hydroxypropylphenyl group, a hydroxybutylphenyl group, a hydroxyl-tert-butylphenyl group, a hydroxypentylphenyl group, a hydroxyisopentylphenyl group, a hydroxyhexylphenyl group, a hydroxyheptylphenyl group, a hydroxyoctylphenyl group, a hydroxynonylphenyl group, a hydroxydecylphenyl group, a hydroxyundecylphenyl group, a hydroxydodecylphenyl group, a hydroxytridecylphenyl group, a hydroxytetradecylphenyl group, etc.

The above hydroxyalkylaryl group may have carbonyl groups of usually 1 to 5, preferably 1 to 2 and more preferably 1 in its chain or at an end of its chain, and/or oxygen atoms of usually 1 to 15, preferably 1 to 10 and more preferably 3 to 5 in its chain or at an end of its chain.

A preferable hydroxyaralkyl group represented by $R^{14}$ having a carbonyl group and/or an oxygen atom includes specifically, for example,

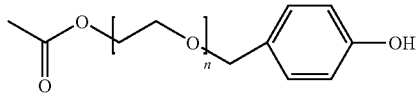

(wherein n is the same as the above.)

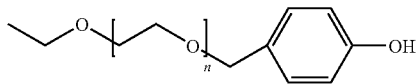

(wherein n is the same as the above.)

An acyloxy group represented by $R^{14}$ may be straight chain, branched or cyclic and includes a group having usually 2 to 6 carbon atoms and preferably 2 to 4 carbon atoms, and specifically an acetyloxy group, a propionyloxy group, a butyryloxy group, a valeryloxy group, a hexanoyloxy group, etc.

An arylacyloxy group represented by $R^{14}$ includes a group having usually 7 to 15 carbon atoms and preferably 7 to 10 carbon atoms, and specifically, for example, a benzoyloxy group and a naphthoyloxy group.

An isocyanatoalkyl group represented by $R^{14}$ maybe straight chain, branched or cyclic and includes a group having usually 2 to 7 carbon atoms and preferably 2 to 5 carbon atoms, and specifically includes a 2-isocyanatomethylphenyl group, a 3-isocyanatomethylphenyl group, a 4-isocyanatomethylphenyl group, an isocyanatoethylphenyl group, an isocyanatopropylphenyl group, an isocyanatobutylphenyl group, an isocyanato-tert-butylphenyl group, an isocyanatopentylphenyl group, an isocyanatoisopentylphenyl group, an isocyanatohexylphenyl group, an isocyanatoheptylphenyl group, an isocyanatooctylphenyl group, an isocyanatononylphenyl group, an isocyanatodecylphenyl group, an isocyanatoundecylphenyl group, an isocyanatododecylphenyl group, an isocyanatotridecylphenyl group, an isocyanatotetradecylphenyl group, etc.

An isocyanatoaryl group represented by $R^{14}$ includes a group having usually 7 to 20 carbon atoms and preferably 7 to 15 carbon atoms, and specifically, for example, an isocyanatophenyl group, an isocyanatonaphthyl group and an isocyanatoanthryl group.

An isocyanatoaralkyl group represented by $R^{14}$ may be straight chain, branched or cyclic and includes a group having usually 8 to 20 carbon atoms and preferably 8 to 15 carbon atoms, and specifically includes a 2-isocyahatophenylmethyl group, a 3-isocyanatophenylmethyl group, a 4-isocyanatophenylmethyl group, an isocyanatophenylethyl group, an isocyanatophenylpropyl group, an isocyanatophenylbutyl group, an isocyanatophenylhexyl group, an isocyanatophenylheptyl group, an isocyanatophenyloctyl group, an isocyanatophenylnonyl group, an isocyanatophenyldecyl group, an isocyanatophenylundecyl group, an isocyanatophenyldodecyl group, an isocyanatophenyltridecyl group, an isocyanatophenyltetradecyl group, etc.

An isocyanatoalkylaryl group represented by $R^{14}$ may be straight chain, branched or cyclic and includes a group having usually 8 to 20 carbon atoms and preferably 8 to 15 carbon atoms, and specifically includes a 2-isocyanatomethylphenyl group, a 3-isocyanatomethylphenyl group, a 4-isocyanatomethylphenyl group, an isocyanatoethylphenyl group, an isocyanatopropylphenyl group, an isocyanatobutylphenyl group, an isocyanato-tert-butylphenyl group, an isocyanatopentylphenyl group, an isocyanatoisopentylphenyl group, an isocyanatohexylphenyl group, an isocyanatoheptylphenyl group, an isocyanatooctylphenyl group, an isocyanatononylphenyl group, an isocyanatodecylphenyl group, an isocyanatoundecylphenyl group, an isocyanatododecylphenyl group, an isocyanatotridecylphenyl group, an isocyanatotetradecylphenyl group, etc.

An aminoalkyl group represented by $R^{14}$ may be straight chain, branched or cyclic and includes a group having usually 2 to 7 carbon atoms and preferably 2 to 5 carbon atoms, and specifically includes a 2-aminomethylphenyl group, a 3-aminomethylphenyl group, a 4-aminomethylphenyl group, an aminoethylphenyl group, an aminopropylphenyl group, an aminobutylphenyl group, an amino-tert-butylphenyl group, an aminopentylphenyl group, an aminoisopentylphenyl group, an aminohexylphenyl group, an aminoheptylphenyl group, an aminooctylphenyl group, an aminononylphenyl group, an aminodecylphenyl group, an aminoundecylphenyl group, an aminododecylphenyl group, an aminotridecylphenyl group, an aminotetradecylphenyl group, etc.

An aminoaryl group represented by $R^{14}$ includes a group having usually 7 to 20 carbon atoms and preferably 7 to 15 carbon atoms, and specifically, for example, an aminophenyl group, an aminonaphthyl group and an aminoanthryl group.

An aminoaralkyl group represented by $R^{14}$ may be straight chain, branched or cyclic and includes a group having usually 8 to 20 carbon atoms and preferably 8 to 15 carbon atoms, and specifically a 2-aminophenylmethyl group, a 3-aminophenylmethyl group, a 4-aminophenylmethyl group, an aminophenylethyl group, an aminophenylpropyl group, an aminophenylbutyl group, an aminophenylhexyl group, an aminophenylheptyl group, an aminophenyloctyl group, an aminophenylnonyl group, an aminophenyldecyl group, an aminophenylundecyl group, an aminophenyldodecyl group, an aminophenyltridecyl group, an aminophenyltetradecyl group, etc.

An aminoalkylaryl group represented by $R^{14}$ may be straight chain, branched or cyclic and includes a group having usually 8 to 20 carbon atoms and preferably 8 to 15 carbon atoms, and specifically a 2-aminomethylphenyl group, a 3-aminomethylphenyl group, a 4-aminomethylphenyl group, an aminoethylphenyl group, an aminopropylphenyl group, an aminobutylphenyl group, an amino-tert-butylphenyl group, an aminopentylphenyl group, an aminoisopentylphenyl group, an aminohexylphenyl group, an aminoheptylphenyl group, an aminooctylphenyl group, an aminononylphenyl group, an aminodecylphenyl group, an aminoundecylphenyl group, an aminododecylphenyl group, an aminotridecylphenyl group, an aminotetradecylphenyl group, etc.

In the above hydroxyaryl group, hydroxyalkyl group, hydroxyalkylaryl group, arylacyloxy group, isocyanatoaryl group, isocyanatoaralkyl group, isocyanatoalkylaryl group, aminoaryl group, aminoaralkyl group, aminoalkylaryl group, etc., an alkyl group which is used as a substituent that an aromatic ring may have, may be straight chain or branched, and includes usually a group having 1 to 4 carbon atoms and specifically a methyl group, an ethyl group, an n-propyl group, an isopropyl group, an n-butyl group, an isobutyl group, a sec-butyl group, a tert-butyl group, etc., and an alkoxy group which is used as a substituent that the aromatic ring may have, may be straight chain or branched, and includes usually a group having 1 to 4 carbon atoms and specifically a methoxy group, an ethoxy group, a propoxy group, an isopropoxy group, a butoxy group, an isobutoxy group, a sec-butoxy group, a tert-butoxy group, etc. A halogen atom which is used as a substituent that an aromatic ring may have, includes, for example, a chlorine atom, a fluorine atom, a bromine atom and an iodine atom.

The above substituents of usually 1 to 5 and preferably 1 to 2 may be present in an aromatic ring in a hydroxyaryl group, a hydroxyaralkyl group, a hydroxyalkylaryl group, an arylacyloxy group, an isocyanatoaryl group, an isocyanatoaralkyl group, an isocyanatoalkylaryl group, an aminoaryl group, an aminoaralkyl group, an aminoalkylaryl group, etc., represented by $R^{14}$.

In a monomer represented by the general formula [5], $R^{14}$ represents preferably a hydroxyalkyl group that may have a carbonyl group and/or an oxygen atom and more preferably a straight chain hydroxyalkyl group that may have an oxygen atom. $R^{14}$, which is a group having an oxygen atom, has oxygen atoms of usually 1 to 15, preferably 1 to 10 and more preferably 3 to 5 in the alkyl chain thereof.

An alkyl group represented by $R^{15}$ in the general formula [5] may be straight chain, branched or cyclic and includes a group having usually 1 to 6 carbon atoms, preferably 1 to 4 carbon atoms and more preferably 1 to 2 carbon atoms, and specifically includes a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a cyclopropyl group, a cyclopentyl group, a cyclohexyl group, etc.

An aryl group represented by $R^{15}$ includes a group having usually 6 to 10 carbon atoms and preferably 6 carbon atoms, and specifically, for example, a phenyl group and a naphthyl group.

An aralkyl group represented by $R^{15}$ may be straight chain, branched or cyclic and includes a group having usually 7 to 12 carbon atoms and preferably 7 to 10 carbon atoms, and specifically a benzyl group, a phenylethyl group, a phenylpropyl group, a phenylbutyl group, a phenylpentyl group, a phenylhexyl group, etc.

A preferable monomer represented by the general formula [5] includes specifically, for example,

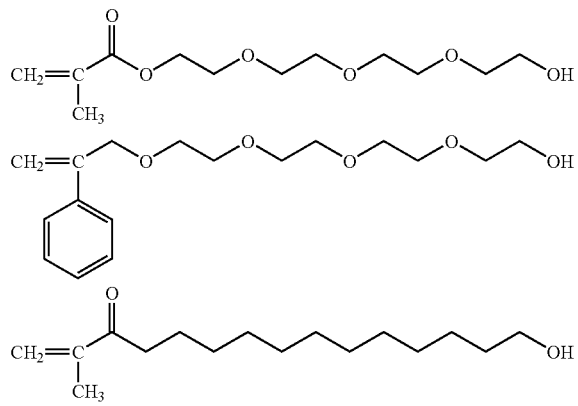

Among these,

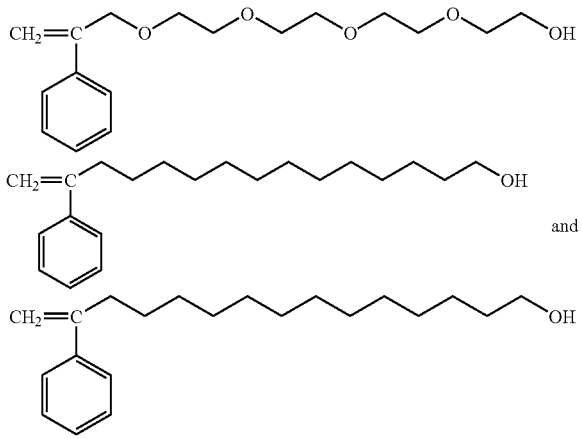

are particularly preferable.

2) A monomer having a polymerizable double bond, which is a raw material for synthesizing a straight chain organic polymer compound which is a copolymer before crosslinking to a crosslinked organic polymer compound relating to the present invention includes, for example, a monomer represented by the following general formula [6]:

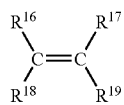

(wherein $R^{16}$ and $R^{17}$ each independently represents a hydrogen atom or an alkyl group having 1 to 6 carbon atoms; $R^{19}$ represents a hydrogen atom, a halogen atom or an alkyl group having 1 to 6 carbon atoms; $R^{18}$ represents a carboxyl group, a hydroxyl group, an acyloxy group having 2 to 6 carbon atoms, an arylacyloxy group having 7 to 15 carbon atoms, an alkoxycarbonyl group having 2 to 6 carbon atoms, an alkyl group having 1 to 6 carbon atoms, an aryl group having 6 to 10 carbon atoms and an aralkyl group having 7 to 12 carbon atoms; an aromatic ring in the above arylacyloxy group, aryl group and aralkyl group may have further an alkyl group having 1 to 4 carbon atoms, an alkoxy group having 1 to 4 carbon atoms or a halogen atom, as a substituent).

An alkyl group represented by $R^{16}$ to $R^{19}$ in the general formula [6] may be straight chain, branched or cyclic and includes a group having usually 1 to 6 carbon atoms, preferably 1 to 4 carbon atoms and more preferably 1 to 2 carbon atoms, and specifically includes a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a cyclopropyl group, a cyclopentyl group, a cyclohexyl group, etc.

A halogen atom represented by $R^{19}$ includes, for example, a chlorine atom, a fluorine atom, a bromine atom and an iodine atom.

An acyloxy group represented by $R^{18}$ may be straight chain, branched or cyclic and includes a group having usually 2 to 6 carbon atoms and preferably 2 to 4 carbon atoms, and specifically includes an acetyloxy group, a propionyloxy group, a butyryloxy group, an isobutyryloxy group, a valeryloxy group, an isovaleryloxy group, a pivaloyloxy group, etc.

An arylacyloxy group represented by $R^{18}$ includes a group having usually 7 to 15 carbon atoms and preferably 7 to 10 carbon atoms, and specifically, for example, a benzoyloxy group and a naphthoyloxy group, etc.

An alkoxycarbonyl group represented by $R^{18}$ may be straight chain, branched or cyclic and includes a group having usually 2 to 6 carbon atoms and preferably 2 to 4 carbon atoms, and specifically includes a methoxycarbonyl group, an ethoxycarbonyl group, a propoxycarbonyl group, an isopropoxycarbonyl group, a butoxycarbonyl group, an isobutyloxycarbonyl group, a sec-butyloxycarbonyl group, a tert-butyloxycarbonyl group, a pentyloxycarbonyl group, an isopentyloxycarbonyl group, a sec-pentyloxycarbonyl group, a tert-pentyloxycarbonyl group, a cyclopropyloxycarbonyl group, a cyclopentyloxycarbonyl group, etc.

An aryl group represented by $R^{18}$ includes a group having usually 6 to 10 carbon atoms and preferably 6 carbon atoms, and specifically, for example, a phenyl group and a naphthyl group.

An aralkyl group represented by $R^{18}$ may be straight chain, branched or cyclic and includes a group having usually 7 to 12 carbon atoms and preferably 7 to 10 carbon atoms, and specifically a benzyl group, a phenylethyl group, a phenylpropyl group, a phenylbutyl group, a phenylpentyl group, a phenylhexyl group, etc.

An alkyl group which is used as a substituent that an aromatic ring in the above arylacyloxy group, aryl group and aralkyl group represented by $R^{18}$ may have, may be straight chain or branched and includes usually a group having 1 to 4 carbon atoms, and specifically a methyl group, an ethyl group, an n-propyl group, an isopropyl group, an n-butyl group, an isobutyl group, a sec-butyl group, a tert-butyl group, etc. An alkoxy group, which is used as a substituent that an aromatic ring in the above 3 groups may have, may be straight chain or branched and includes usually a group having 1 to 4 carbon atoms, and specifically a methoxy group, an ethoxy group, a propoxy group, an isopropoxy group, a butoxy group, an isobutoxy group, a sec-butoxy group, a tert-butoxy group, etc. A halogen atom which is used as a substituent that an aromatic ring in the above 3 groups may have, includes, for example, a chlorine atom, a fluorine atom, a bromine atom and an iodine atom.

The above substituents of usually 1 to 5 and preferably 1 to 2 may be present in an aromatic ring in the hydroxyaryl group, hydroxyaralkyl group and hydroxylalkylaryl group represented by $R^{18}$.

$R^{18}$ in a monomer represented by the general formula [6] is preferably an aryl group and more preferably a phenyl group, and such a monomer is also called a styrene-based monomer in the present invention.

A preferable styrene-based monomer includes specifically styrene, α-methylstyrene, β-methylstyrene, α-ethylstyrene, o-methylstyrene, m-methylstyrene, p-methylstyrene, etc., and among these, styrene and α-methylstyrene are more preferable and styrene is particularly preferable.

At least one monomer among 1) the above monomers represented by the general formulas [1], [2], [4] and [5], having a crosslinkable functional group and a polymerizable double bond and 2) the above monomers represented by the general formula [6], having a polymerizable double bond, preferably has an aromatic ring in the molecule thereof. Among them, more preferably, a monomer represented by the general formula [6] has an aromatic ring therein and, further preferably, all monomers have an aromatic ring.

A crosslinked organic polymer compound relating to the present invention is preferably a compound obtained by crosslinking a copolymer of (1) a glycidyl compound having an epoxy group and a polymerizable double bond, (2) a styrene-based monomer and (3) an acrylic-acid-based monomer or a monomer having a hydroxyalkyl group containing one or more oxygen atoms and a polymerizable double bond. Among these monomers, (3) a monomer having a hydroxyalkyl group containing one or more oxygen atoms and a polymerizable double bond is more preferable. A compound is further preferable that is obtained by crosslinking (1) a copolymer of a glycidyl compound having an aromatic ring, an epoxy group and a polymerizable double bond, (2) a styrene-based monomer and (3) a monomer having an aromatic ring, a hydroxyalkyl group containing one or more oxygen atoms and a polymerizable double bond. That is, it is desirable for each monomer unit to have an aromatic ring, and monomer units of usually 50% or more, preferably 70% or more and more preferably 100% based on all monomer units may have an aromatic ring.

A polymer or a copolymer obtained by polymerizing or copolymerizing one or more kinds of the above 1) monomers having a crosslinkable functional group and a polymerizable double bond, or a copolymer obtained by copolymerizing one or more kinds of 1) monomers having a crosslinkable functional group and a polymerizable double bond and one or more kinds of monomers 2) having a polymerizable double bond, is sometimes abbreviated as a straight chain organic polymer compound.

A straight chain organic polymer compound having a crosslinkable functional group may be obtained by a well known polymerization method, wherein various monomers described above are dissolved or suspended in a proper solvent, followed by the addition of a suitable polymerization initiator and reacting while stirring and heating.

For example, an objective straight chain organic polymer compound can be obtained by mixing various monomers described above in ratio described above, followed by dissolving the monomers in a proper solvent of 1 to 10 times as much as the monomers' volume, such as toluene, 1,4-dioxane, tetrahydrofuran, isopropanol, methyl ethyl ketone, etc., reacting the monomers at 50 to 150° C. for 1 to 20 hours in nitrogen stream in the presence of a polymerization initiator of 0.1 to 30% by weight based on the monomers, such as azoisobutyronitrile, 2,2'-azobis(2,4-dimethylvaleronitrile), 2,2'-azobis(2-methylpropionic acid methyl ester), 2,2'-azobis(2-methylbutyronitrile), benzoyl peroxide, lauroyl peroxide, etc., and subjecting the reaction mixture to the post process according to an ordinary method for obtaining a polymer.

Weight average molecular weight (Mw) of a straight chain organic polymer compound relating to the present invention is not especially limited as long as the compound is soluble in a proper solvent, and is usually 2,000 to 3,000,000 and preferably 10,000 to 100,000.

A monomer unit constituting the above straight chain organic polymer compound includes a monomer unit represented by the following general formula [1'] that is derived from a monomer represented by the above general formula [1]:

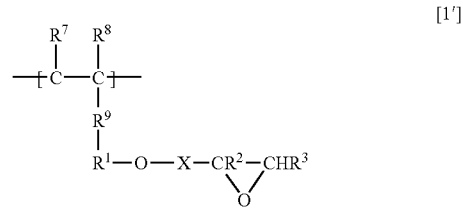

[1']

(wherein $R^1$ to $R^3$ and $R^7$ to $R^9$ are the same as the above), a monomer unit represented by the following general formula [2'] that is derived from a monomer represented by the above general formula [2]:

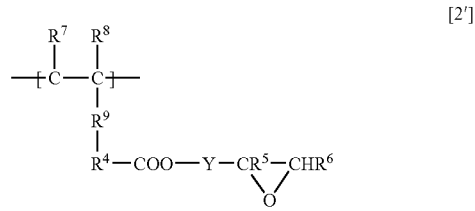

[2']

(wherein $R^4$ to $R^9$ are the same as the above), a monomer unit represented by the following general formula [4'] that is derived from a monomer represented by the above general formula [4]:

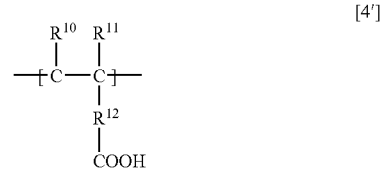

[4']

(wherein $R^{10}$ to $R^{12}$ are the same as the above), a monomer unit represented by the following general formula [5'] that is derived from a monomer represented by the above general formula [5]:

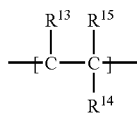

(wherein R$^{13}$ to R$^{15}$are the same as the above), and a monomer unit represented by the following general formula [6'] that is derived from a monomer represented by the above general formula [6]:

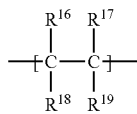

(wherein, R$^{16}$ to R$^{19}$ are the same as the above)

When a combination of various monomer units constituting a straight chain organic polymer compound relating to the present invention is, for example, (1) a glycidyl compound having an epoxy group and a polymerizable double bond, (2) a styrene-based monomer and (3) an acrylic-acid-based monomer, a straight chain organic polymer compound having the above ratio of the monomer units represented by the general formula [1'] or [2'], and the general formula [4'] is synthesized, since the monomer units among the monomer units represented by the general formula [1'] or [2'], general formula [6'] and general formula [4'] that correspond to above monomers respectively, have a crosslinkable functional group. When the combination is (1) a glycidyl compound having an epoxy group and a polymerizable double bond, (2) a styrene-based monomer and (3) a monomer having a hydroxyalkyl group containing one or more oxygen atoms and a polymerizable double bond, a straight chain organic polymer compound having the above ratio of monomer units represented by the general formula [1'] or [2'], and the general formula [5'] is similarly synthesized. Ratio of (1) a glycidyl compound having an epoxy group and a polymerizable double bond, (2) a styrene-based monomer and (3) a monomer having a hydroxyalkyl group containing one or more oxygen atoms and a polymerizable double bond is preferably (1):(2):(3)=3 to 12:78 to 92:5 to 10.

In a so-called crosslinked organic polymer compound relating to the present invention, obtained by crosslinking a copolymer composed from monomer units represented by the above general formulas [1'], [2'], [4'], [5'] and/or [6'], a crosslinking section exists between an alkylene chain derived from a polymerizable double bond and another alkylene chain derived from a polymerizable double bond, which are represented by the following structural formula existing in a monomer unit:.

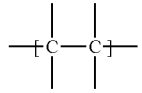

Number of atoms in the shortest chain of the above crosslinking section in the present invention is usually one or more. The preferable lower limit thereof is, in order, 2, 3, 5, 8, 10, 11, 15, 18 and 19 (the latter is more preferable), and the preferable upper limit thereof is in order, 400, 200, 100, 80, 70, 60, 50, 45, 40, 35, 30 and 28 (the latter is more preferable).

The above number of atoms in the shortest chain of a crosslinking section is, for example, 9, as shown by numbering in structural formula, when the crosslinking section of a polymer compound has structure represented as follows:

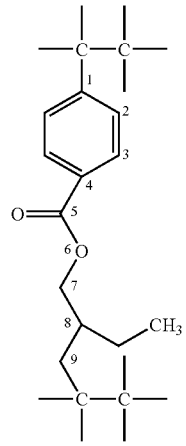

A catalyst composition of the present invention, where a palladium catalyst is physically carried on the crosslinked organic polymer compound such as described above, can be manufactured by homogenizing, for example, a straight chain organic polymer compound having a crosslinkable functional group and a palladium catalyst in a solvent dissolving said straight chain organic polymer compound, followed by depositing a composition formed and subjecting the crosslinkable functional group in said deposit composition to condensation for crosslinking reaction. Additionary, in the above manufacture, a palladium catalyst is not necessary to be dissolved in a solvent as long as it is uniformly suspended. It is also possible to prepare an objective catalyst composition of the present invention even from such condition.

It has been found that a palladium catalyst carried on a catalyst composition of the present invention is converted to Pd(0) itself without any coordinated ligand, when Pd(0) coordinated by a ligand (hereinafter, sometimes abbreviated to coordinated Pd(0)) is used as a palladium catalyst, and also a combination of suitable crosslinkable functional groups is subjected to a crosslinking reaction so that number of atoms in the shortest chain of the final crosslinking section may be 10 to 35 and preferably 15 to 30. It has been believed that Pd(0) itself is too extremely unstable to be taken out in stable state, however, a catalyst composition physically carrying Pd(0) itself can be easily obtained (without, for example, reduction treatment) by carrying out a method of the present invention, by combining a specific palladium catalyst (coordinated Pd(0)) and a straight chain organic polymer compound having the above mentioned specific crosslinkable functional group. A preferable combination of crosslinkable functional groups to be used for the above purpose includes, for example, a combination of a glycidyl group having an epoxy group in a monomer represented by the general formula [1] or [2] and a hydroxyalkyl group that may contain a carbonyl group or/and an oxygen atom, represented by R$^{14}$ in a monomer represented by the general formula [5]. A ligand to be used for the above purpose includes 1,5-cyclooctadiene (COD), dibenzylideneacetone (DBA), bipyridine (BPY), phenanthrbline (PHE), benzonitrile (PhCN), isocyanide (RNC), triethylarsine (As(Et$_3$)), organic phosphine ligands such as dimethylphenylphosphine (P(CH$_3$)$_2$Ph), diphenylphosphinoferrocene (dPPf), trimethylphosphine (P(CH$_3$)$_3$), triethylphosphine (P(Et)$_3$), tri-tert-butylphosphine (P($^t$-Bu)$_3$), tricyclohexylphosphine (PCy$_3$), trimethoxyphosphine (P(OCH$_3$)$_3$), triethoxyphosphine (P(OEt)$_3$), tri-tert-butoxyphosphine (P(O$^t$-Bu)$_3$), triphenylphosphine (PPh$_3$), 1,2-bis(diphenylphosphino) ethane (DPPE), triphenoxyphosphine (P(OPh)$_3$), etc., and among these, an organic phosphine ligand is preferable and triphenylphosphine, tri-tert-butylphosphine, triethylphosphine, trimethylphosphine, and the like are particularly preferable, and triphenylphosphine is more preferable among them. It is not clear why such phenomenon occurs, but it is considered that crosslinking the above specific crosslinkable functional group causes steric hindrance, leading to elimination of a ligand from coordinated Pd(0).

A carried amount of a palladium catalyst is usually 0.00001 to 0.01 mol and preferably 0.00005 to 0.005 mol based on 1 g of a crosslinked polymer compound, while an amount of a palladium metal carried on a crosslinked polymer compound is usually 0.00001 to 50% by weight, preferably 0.0001 to 30% by weight, more preferably 0.001 to 15% by weight and still more preferably 0.01 to 10% by weight based on a crosslinked polymer compound.

A solvent to dissolve a straight chain organic polymer compound having the above crosslinkable functional group includes ethers such as tetrahydrofuran, etc.: hydrocarbons such as cyclohexane, n-hexane, etc.: halogenated hydrocarbons such as methylene chloride, etc.

Temperature on dissolving a straight chain organic polymer compound having a crosslinkable functional group in the above solvent, is usually –78 to 200° C., preferably –20 to 100° C. and more preferably 0 to 50° C.

A palladium catalyst is physically carried on a straight chain organic polymer compound having a crosslinkable functional group by homogenizing the straight chain organic polymer compound having a crosslinkable functional group and the palladium catalyst in the above solvent.

The above physically carrying state is different from carrying by so-called chemical bond such as an ionic bond and a covalent bond, and is simple fixation (carrying), that is, state that a palladium catalyst is sandwiched or enveloped by molecular chains of a straight chain organic polymer compound.

A composition obtained by filtering a composition deposited in a solvent, in which a palladium catalyst is physically carried on a straight chain organic polymer compound having a crosslinkable functional group, is heated, for example, without using a solvent and thus various crosslinkable functional groups contained in the above composition cause crosslinking reaction to form crosslinkages. Degree of the resultant crosslinkage is not especialy limited as long as it does not impair objective catalyst activity, and the crosslinked monomer units are about 0.1 to 10%, preferably about 0.5 to 5% and more preferably about 0.5 to 3% based on the total monomer units.

Exception of the above method by heating, a crosslinking reaction relating to the present invention can be carried out according to conventionally known methods used for crosslinking a straight chain organic polymer compound, such as a method to use a crosslinking agent, a method to use a condensing agent, a method to use a radical-polymerization catalyst such as a peroxide and an azo compound, a method to add an acid and then to heat, and a method to react by combination of a dehydrocondensation agent such as carbodiimides and an appropriate crosslinking agent.

The state of physically carrying in the palladium catalyst is a network structure formed by closslinking the polymer as a carrier. The network structure gives stronger physical fixation (carrying) of a palladium catalyst than the above mentioned physical carrying of a metal catalyst given by a straight chain polymer compound, resulting in less leaking of a palladium catalyst.

Crosslinking temperature of a crosslinkable functional group by heating is, usually at 50 to 300° C., preferably 70 to 200° C. and more preferably 100 to 180° C.

Reaction period on thermal crosslinking is usually 0.1 to 100 hours, preferably 1 to 50 hours and more preferably 3 to 10 hours.

When crosslinking is carried out by a crosslinking agent, the crosslinking agent for a polymer having an epoxy group as a crosslinkable functional group: polyamine compounds such as hexamethylenediamine, hexamethylenetetramine, etc.; polyol compounds such as ethylene glycol, propylene glycol, glycerine, etc.; polycarboxylic acids and their anhydrides such as malonic acid, succinic acid, glutaric acid, adipic acid, pimelic acid, maleic acid, fumaric acid, etc., the closslinking agent for a polymer having a carboxyl group as a crosslinkable functional group: polyhydroxy compounds such as ethylene glycol, glycerine, etc.; alkylene oxides such as ethylene oxide, propylene oxide, etc., the closslinking agent for a polymer having a hydroxyl group and/or an acyloxy group as a crosslinkable functional group: polycarboxylic acids and their anhydrides such as malonic acid, succinic acid, glutaric acid, adipic acid, pimelic acid, maleic acid, fumaric acid, etc.; alkylene oxides such as ethylene oxide, propylene oxide, etc.; polyamine compounds such as hexamethylenediamine, hexamethylenetetramine, etc., the closslinking agent for a polymer having monomer unites derived from a monomer having an isocyanato group as a crosslinkable functional group: polyhydroxy compounds such as water, ethylene glycol, glycerine, etc.; polycarboxylic acids and their anhydrides such as malonic acid, succinic acid, glutaric acid, adipic acid, pimelic acid, maleic acid, fumaric acid, etc.; polyamine compounds such as hexamethylenediamine, hexamethylenetetramine, etc., and the closslinking agent for a polymer with an amino group as a crosslinkable functional group: polycarboxylic acids and their anhydrides such as malonic acid, succinic acid, glutaric acid, adipic acid, pimelic acid, maleic acid, fumaric acid, etc.; alkylene oxides such as ethylene oxide, propylene oxide, etc.

When crosslinking is carried out using a condensing agent, the condensing agent includes, for example, a dehydrating agent belonging to carbodiimides such as dicyclohexyl carbodiimide for a polymer having a carboxyl group as a crosslinkable functional group.

Structure type at crosslinked section formed by the above mentioned crosslinking reactions include:

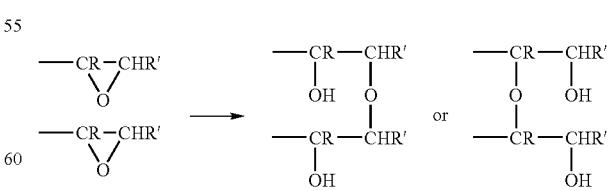

(wherein R represents the above R$^2$ or R$^5$; and R' represents the above R$^3$ or R$^6$) formed by, for example, thermal crosslinking of two epoxy groups which are crosslinkable functional groups;

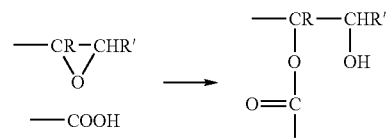

(wherein R represents the above $R^2$ or $R^5$; and R' represents the above $R^3$ or $R^6$) formed by, for example, thermal crosslinking of an epoxy group, which is a condensed functional group, and a carboxyl group;

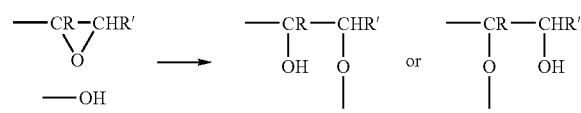

(wherein R represents the above $R^2$ or $R^5$; and R' represents the above $R^3$ or $R^6$) formed by, for example, thermal crosslinking of an epoxy group, which is a condensed functional group, and a hydroxyl group;

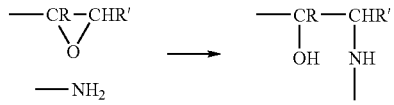

(wherein R represents the above $R^2$ or $R^5$; and R' represents the above $R^3$ or $R^6$) formed by, for example, thermal crosslinking of an epoxy group, which is a condensed functional group, and an amino group;

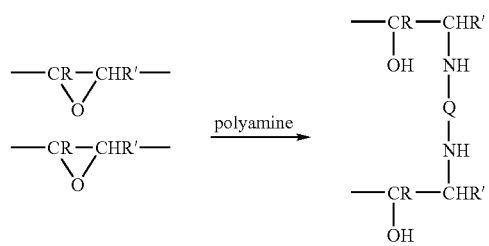

(wherein R represents the above $R^2$ or $R^5$; R' represents the above $R^3$ or $R^6$; and —NH-Q-NH— represents a group derived from a polyamine) formed by, for example, crosslinking of two epoxy groups, which are condensed functional groups, using an amino group of a polyamine crosslinking agent;

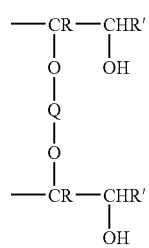

(wherein R represents the above $R^2$ or $R^5$; R' represents the above $R^3$ or $R^6$; and —O-Q-O— represents a group derived from a diol) formed by, for example, crosslinking of two epoxy groups, which are crosslinkable functional groups, using a polyol crosslinking agent;

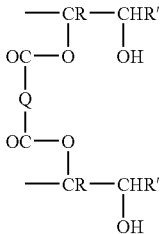

(wherein R represents the above $R^2$ or $R^5$; R' represents the above $R^3$ or $R^6$; and —O—OC-Q-CO—O— represents a group derived from a polycarboxylic acid) formed by, for example, crosslinking of two epoxy groups, which are crosslinkable functional groups, using a polycarboxylic acid crosslinking agent;

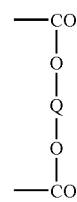

(wherein —O-Q-O— represents a group derived from a polyhydroxyl compound or an alkylene oxide) formed by, for example, crosslinking of two carboxyl groups which are crosslinkable functional groups, using a polyhydroxy compound or an alkylene oxide crosslinking agent;

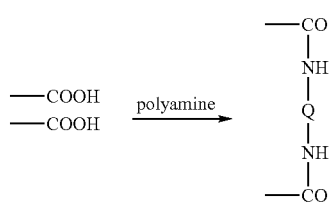

(wherein —HN-Q-NH— represents a group derived from a polyamine) formed by, for example, crosslinking of two carboxyl groups which are crosslinkable functional groups using a polyamine compound crosslinking agent;

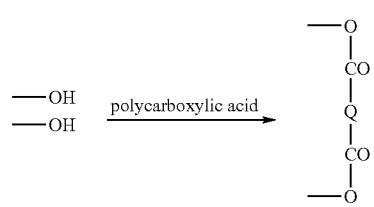

(wherein —OOC-Q-COO— represents a group derived from a polycarboxylic acid) formed by, for example, crosslinking of two hydroxyl groups which are crosslinkable functional groups, using a polycarboxylic acid crosslinking agent;

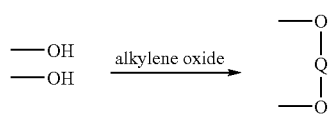

(wherein —O-Q-O— represents a group derived from an alkylene oxide) formed by, for example, crosslinking of two hydroxyl groups which are crosslinkable functional groups using an alkylene oxide crosslinking agent;

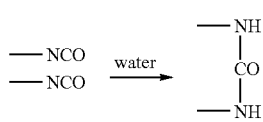

formed by, for example, crosslinking of two isocyanato groups which are crosslinkable functional groups using water;

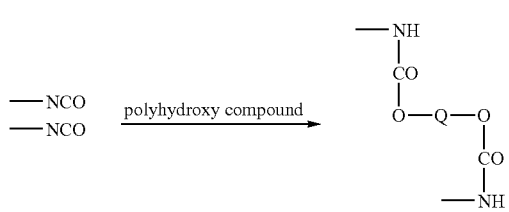

(wherein —O-Q-O— represents a group derived from a dihydroxy compound) formed by, for example, crosslinking of two isocyanato groups, which are crosslinkable functional groups, using a polyhydroxy compound crosslinking agent;

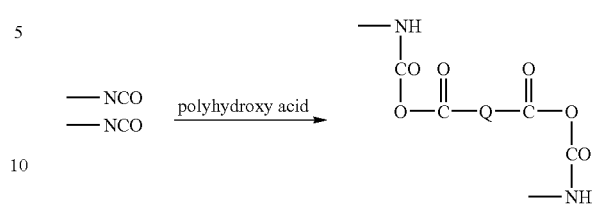

(wherein —O—CO-Q-OC—O— represents a group derived from a dicarboxylic acid) formed by, for example, crosslinking of two isocyanato groups, which are crosslinkable functional groups, using a polycarboxylic acid crosslinking agent;

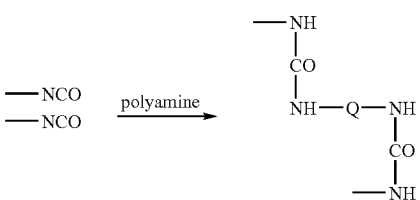

(wherein —HN-Q-NH— represents a group derived from a polyamine) formed by, for example, crosslinking of two isocyanato groups, which are crosslinkable functional groups, using a polyamine crosslinking agent;

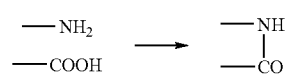

formed by, for example, crosslinking of an amino group and a carboxyl group, which are crosslinkable functional groups, using a dehydrating agent; and

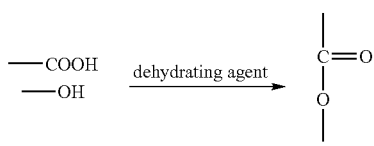

formed by, for example, crosslinking of a hydroxyl group and a carboxyl group, which are crosslinkable functional groups, using a dehydrating agent.

A crosslinked organic polymer compound relating to the present invention may be prepared by using the second polymer compound having a polymerizable double bond as a polymer compound before crosslinking. Such a method includes, for example, carrying out a crosslinking reaction induced by action of a catalyst, for example, a peroxide such as benzoyl peroxide and an azo compound such as 2,2'-azobisisobutyronitrile, in the presence or absence of a monomer having a polymerizable double bond such as maleic anhydride.

A reaction example for producing a crosslinked organic polymer compound of the present invention is shown below, where raw material monomers of vinylglycidyl ether, acrylic acid and styrene are polymerized to obtain a polymer compound before crosslinking, which is then crosslinked.

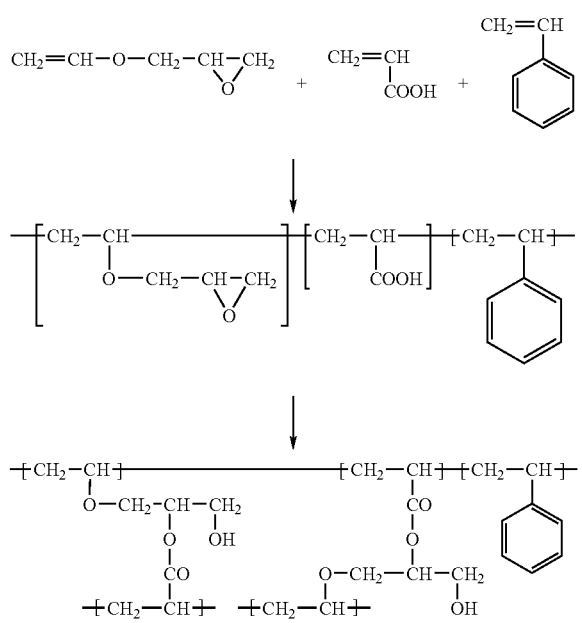

In thus obtained catalyst composition of the present invention, a palladium catalyst is physically carried on a crosslinked organic polymer compound. Consequently, electrons are provided by an aromatic ring in a crosslinked organic polymer compound carrier, in particular, an aromatic ring in a styrene-based monomer unit, which is considered to enhance catalytic activity compared with conventional palladium catalysts.

A catalyst composition of the present invention is very useful as a catalyst for various reactions, because of superior solvent resistance, little leak of a metal catalyst carried on a crosslinked organic polymer compound, no deterioration of catalyst activity even by repeated use and easy handling. Further, a palladium catalyst of 0 valence, in particular, Pd(0) not coordinated, which has not been easily handled, because it may sometimes spontaneously ignite in air or lower its activity in air, can be furnished with higher activity than conventional ones and can be used and stored safely for a long period, in accordance with a catalyst composition of the present invention, where a palladium catalyst is physically carried on a crosslinked organic polymer compound.

Since having superior characteristics mentioned above, a catalyst composition of the present invention can be advantageously used in industry as a catalyst for various chemical reactions.

Hydrogenation (reduction) of a carbon-carbon double bond in a compound having a reactive double bond is one example of these reactions. This means the addition of hydrogen to a reactive carbon-carbon double bond, and for example, an olefin compound is added with hydrogen to get a carbon-carbon single bond, thus leading to easy reduction of the olefin compound, by using a catalyst composition of the present invention as a catalyst.

A compound having a reactive double bond as a reaction substrate includes any compound as long as it has a reactive double bond, for example, a polymer compound and a compound having any functional group and/or aromatic ring as a substituent, as long as these compounds have at least one reactive double bond in a molecule, to say nothing of an olefin compound, a diene compound and an unsaturated cyclic hydrocarbon compound.

Use amount of a catalyst composition of the present invention for a hydrogenation reaction is usually 0.000001 to 50% by weight, preferably 0.00001 to 20% by weight and more preferably 0.001 to 10% by weight based on a reaction substrate.

The above hydrogenation reaction may be carried out either in an appropriate solvent or in non-solvent.

A solvent may be any one as long as it is liquid at reaction temperature, and includes specifically, aliphatic hydrocarbons such as propane, butane, pentane, hexane, heptane, octane, nonane, decane, undeane, dodecane, tridecane, tetradecane, pentadecane, hexadecane, heptadecane, octadecane, nonadecane, icosane, cyclopropane, cyclobutane, cyclopentane, cyclohexane, cycloheptane, etc.; aromatic hydrocarbons such as benzene, naphthalene, etc.; alkyl group substituted aromatic hydrocarbons such as toluene, xylene, mesitylene, ethylbenzene, propylbenzene, cumene, butylbenzene, isobutylbenzene, tert-butylbenzene, pentylbenzene, hexylbenzene, etc.; biphenyl derivatives such as biphenyl, terphenyl, etc.; halogen substituted aromatic hydrocarbons such as fluorobenzene, difluorobenzene, trifluorobenzene, tetrafluorobenzene, pentafluorobenzene, hexafluorobenzene, chlorobenzene, dichlorobenzene, trichlorobenzene, tetrachlorobenzene, pentachlorobenzene, hexachlorobenzene, bromobenzene, dibromobenzene, tribromobenzene, tetrabromobenzene, pentabromobenzene, hexabromobenzene, iodobenzene, diiodobenzene, triiodobenzene, tetraiodobenzene, pentaiodobenzene, hexaiodobenzene, chloronaphthalene, dichloronaphthalene, fluorotoluene, chlorotoluene, bromotoluene, iodotoluene, etc.; alkoxy group substituted aromatic hydrocarbons such as anisole, ethoxybenzene, propyloxybenzene, butoxybenzene, pentyloxybenzene, hexyloxybenzene, etc.; alcohols such as methanol, ethanol, propanol, butanol, pentanol, hexanol, heptanol, octanol, nonanol, decanol, undecanol, dodecanol, tridecanol, tetradecanol, pentadecanol, hexadecanol, benzyl alcohol, etc.; phenol derivatives such as phenol, catechol, resorcinol, cresol, etc.; aliphatic carboxylic acid esters such as methyl formate, ethyl formate, methyl acetate, ethyl acetate, butyl acetate, methyl propionate, ethyl propionate, butyl propionate, ethyl butyrate, ethyl butyrate, ethyl valerate, ethyl hexanoate, dimethyl oxalate, diethyl oxalate, dimethyl malonate, diethyl malonate, dibutyl malonate, dimethyl succinate, diethyl succinate, dimethyl adipate, diethyl pimelate, ethyl acetoacetate, etc.; aromatic carboxylic acids such as methyl benzoate, ethyl benzoate, propyl benzoate, butyl benzoate, etc.; ketones such as acetone, methyl ethyl ketone, diethyl ketone, hexanone, cyclohexylacetone, acetophenone, propiophenone, acetoin, etc.; ethers such as dimethyl ether, methyl ethyl ether, diethyl ether, diisopropyl ether, tert-butyl methyl ether, tetrahydrofuran, tetrahydropyran, 1,4-dioxane, cyclopentyl phenyl ether, etc.; aldehydes such as formaldehyde, acetaldehyde, propionaldehyde, butylaldehyde, isobutylaldehyde, valeraldehyde, isovaleraldehyde, benzaldehyde, anisaldehyde, nicotinaldehyde, glyceraldehyde, glycolaldehyde, malonaldehyde, succinaldehyde, glutaraldehyde, adipinaldehyde, phthalaldehyde, isophthalaldehyde, terephthalaldehyde, glyoxal, aminoacetoaldehyde, aminobutylaldehyde, asparticlaldehyde, etc.; amines such as ammonia, methylamine, ethylamine, dimethylamine, trimethylamine, diethylamine, triethylamine, 1-ethylbutylamine, cyclohexylamine, naphthylamine, benzofuranamine, etc. These solvents are selected as appropriate depending on such as kind of a reaction substrate, reaction temperature or an objective reaction period, and may be used either alone or in a proper combination of two or more solvents.

It is preferable to use a solvent not comprising a compound having structure to induce a hydrogenation reaction of a carbon-carbon double bond thereof so as to give priority to a hydrogenation reaction of a reaction substrate.

A reaction can be carried out in suspended state, even if a reaction substrate is not completely dissolved in the above solvent.

When a solvent is not used, a reaction substrate may be reacted in molten state or in vapor phase.

Reaction temperature is usually −30 to 300° C., preferably 0 to 200° C. and more preferably 20 to 200° C.

Reaction period is usually 0.1 to 200 hours, preferably 0.2 to 24 hours and more preferably 1 to 12 hours.

Reaction pressure is usually atmospheric pressure to 100 MPa, preferably atmospheric pressure to 10 MPa and more preferably atmospheric pressure to 1 MPa.

With regard to reaction conditions other than the conditions described above, and a method for post processing, those in accordance with known hydrogenation reactions may be adopted.

The above hydrogenation reaction, in which a catalyst composition of the present invention is used as a catalyst, is shown by the following reaction scheme, taking benzalacetone as an example of olefin.

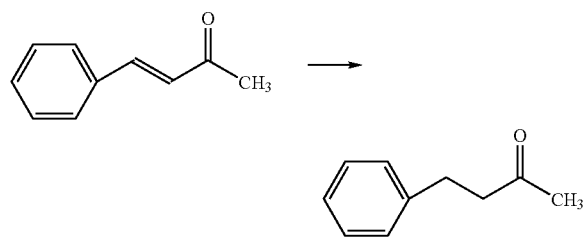

Metal catalysts of 0 valence such as platinum, palladium, ruthenium, iridium and Raney nickel have been used in a hydrogenation reaction of an olefin, and the like as a heterogeneous catalyst, which is insoluble in a reaction solvent. In this connection, platinum has been used in $PtO_2$ form and other metals have been used in carried state on an inert inorganic carrier such as activated carbon, alumina, barium sulfate and calcium carbonate. Among these, palladium fixed on activated carbon (palladium-carbon) has been most frequently used for reduction (hydrogenation) of a carbon-carbon double bond using hydrogen.

However, palladium fixed on activated carbon has a problem wherein the fixed metal leaks during use and cannot be reused.

The above catalyst composition of the present invention has equivalent or higher activity than a conventional palladium-carbon catalysts and easily handled, and also keeps its activity in repeated use of many times with little metal leakage, and therefore is very useful as a catalyst for the above hydrogenation reaction of an olefin, and the like.

A catalyst composition of the present invention is also useful for reduction of a carbonyl group, a halogen, a nitro group, a nitrile group, and the like, in addition to hydrogenation of an olefin, etc.

A catalyst composition of the present invention is also useful as a catalyst for so-called substitution reaction at an allyl position.

An allyl carbonate and a carbon nucleophilic agent are dissolved in a proper solvent and a proper ligand (for example, triphenylphosphine) is added thereto and then the obtained solution is subjected to a reaction under stirring in the presence of a catalyst composition of the present invention, to obtain a compound where the carbon nucleophilic agent substitutes at carboxyl ester position of an allyl carbonate.

A substitution reaction at the above allyl position, where allyl methyl carbonate is used as an allyl carbonate and phenyl dimethyl malonate is used as a carbon nucleophilic agent are used, is shown by reaction scheme below.

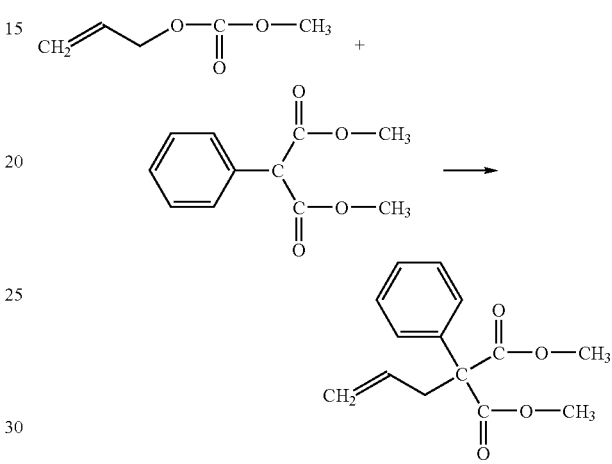

A catalyst composition of the present invention to be used in a substitution reaction at the above allyl position preferably comprises a crosslinked organic polymer compound not having an ester linkage.

An allyl carbonate in reaction substrates in a substitution reaction at the allyl position of the present invention includes, allyl methyl carbonate, allyl ethyl carbonate, allyl propyl carbonate, allyl phenyl carbonate, etc.

A carbon nucleophilic agent includes a compound of low electron-density such as methylene chloride, malonic acid ester, cyanoacetic acid ester, activated carbon, etc.

A ligand to be added on a reaction includes, organic phosphine ligands such as triphenylphosphine, tri-tert-butylphosphine, triethylphosphine, trimethylphosphine, and the like and among these, triphenylphosphine is preferable.

A reactive solvent is not especially limited as long as the solvent can be used in this field.

Reaction temperature is usually −78 to 200° C., preferably −20 to 100° C. and more preferably 0 to 50° C.

Reaction period is usually 0.1 to 200 hours, preferably 0.2 to 24 hours and more preferably 1 to 12 hours.

A reaction similar to the above reaction can be carried out in high yield, by using a catalyst composition of the present invention as a catalyst, wherein a crosslinked organic polymer compound has an aromatic ring such as a styrene monomer unit, and also using an oxygen nucleophilic agent such as phenol having an electron acceptor group such as a phenol group, and further a nitro group and a cyano group, instead of the above carbon nucleophilic agent.

It has been known that reactivity of a reaction using an oxygen nucleophilic agent, such as phenol having an electron acceptor group, is remarkably lowered compared with that of the above substitution reaction at the allyl position using a carbon nucleophilic agent. Therefore, it is estimated that in the above catalyst composition of the present invention, an electron is donated to a carried metal catalyst by an aromatic ring of a styrene monomer unit existing in the carrier part of the catalyst composition, that is, a crosslinked organic polymer compound, leading to improved activity of the catalyst itself.

A catalyst composition of the present invention is also useful as an oxidation catalyst of alcohols.

For example, in oxidation of secondary alcohols and allyl-type alcohols, such alcohols react first with allyl carbonate to form an allyl carbonate (that is, diester), which are reacted in a proper solvent in the presence of a catalyst composition of the present invention, to induce beta elimination to form a ketone, as a result, the secondary alcohol and the allyl-type alcohol are oxidized.

An allyl-type alcohol in the above oxidation of alcohols includes, allyl alcohol, crotyl alcohol, cinnamyl alcohol, etc.

A primary alcohol such as cinnamyl alcohol can be oxidized using a catalyst composition of the present invention as a catalyst in a "one-pot reaction" as shown by reaction scheme below.

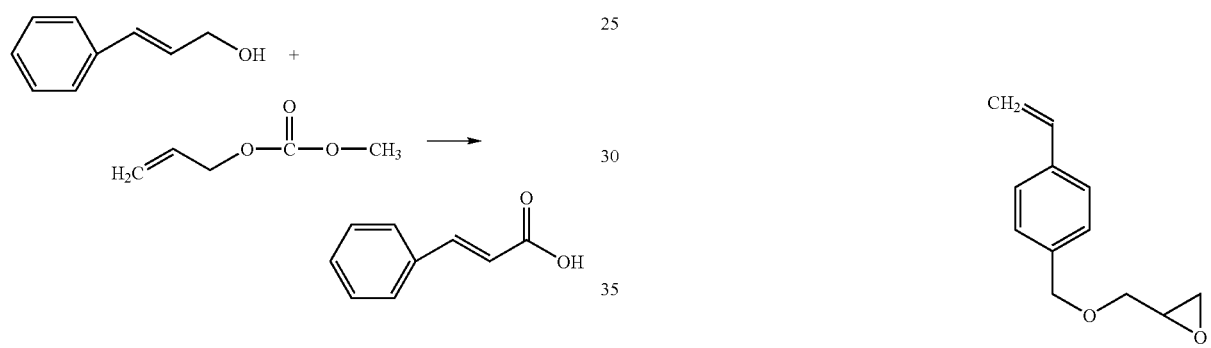

As described above, when triphenylphosphine is present in a system of a reaction using an allyl carbonate, a substitution reaction at the allyl position proceeds, while an oxidation reaction does not. From the fact that in the above oxidation reaction of cinnamyl alcohol, no substitution reaction at the allyl position occurs even by using a catalyst composition of the present invention, while objective oxidation of the alcohol proceeds, it can be confirmed that no phosphine ligand is contained in a catalyst composition of the present invention, although a catalyst composition of the present invention is produced from a metal catalyst coordinated with a phosphine ligand as a raw material.

As described above, a catalyst composition of the present invention, where a palladium catalyst is physically carried on a crosslinked organic polymer compound, obtained by homogenizing a straight chain organic polymer compound having a crosslinkable functional group and the palladium catalyst in a solvent dissolving these, followed by depositing a composition formed and subjecting the crosslinkable functional group in said deposit composition to condensation for crosslinking reaction, can be handled safely and easily without danger of spontaneous ignition and is very useful as a catalyst for various reactions and also has advantage that it keeps its activity even in repeated use and a metal catalyst does not leak from its polymer compound carrier. It has been said that a heterogeneous catalyst such as a catalyst composition of the present invention generally has lower activity, however, a catalyst composition of the present invention has surprising effect of rather higher catalyst activity than a conventional catalyst.

The present invention will be described hereinbelow in more detail with Examples and Comparative Examples, which do not constitute limiting aspects of the present invention.

EXAMPLE

Referential Example 1

Synthesis of a Glycidyl Compound

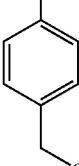

After washing 4.00 g of sodium hydride (purity: 60%) with petroleum ether, it was dried under reduced pressure, and 200 ml of dimethylformamide was added thereto, and cooled in an ice bath. Then, 6.6 ml of glycidol was added to the system while stirring, and the reaction solution was reacted while stirring at room temperature for one hour. After completing the reaction, 7 ml of 4-vinylbenzyl chloride and 1.84 g of tetran n-butylammonium iodide were added to the reaction solution while stirring for 5 hours. After completing the reaction, the reaction solution was ice-cooled, and diluted with diethyl ether and then the reaction was terminated by adding a saturated aqueous solution of ammonium chloride. After separating an organic layer of the solution, a water layer was extracted with diethyl ether and it was combined with the organic layer separated, washed with a saturated aqueous solution of sodium bicarbonate and saturated salt water, and dried with sodium sulfate anhydride. After drying, this was filtrated, condensed under reduced pressure and purified by silica gel column chromatography to obtain 6.86 g of 4-vinylbenzyl glycidyl ether (yield: 73%). Measurement results by $^1$H-NMR and $^{13}$C-NMR of 4-vinylbenzyl glycidyl ether obtained are shown below.

$^1$H-NMR (CDCl$_3$) δ=2.60 (d, 1H, J=2.5, 5.1 Hz), 2.57 (d, 1H, J=4.2, 5.1 Hz), 3.17 (dddd, 1H, J=2.7, 2.9, 5.1, 5.7 Hz), 3.41 (dd, 1H, J=5.7, 11.3 Hz), 3.75 (dd, 1H, J=2.9, 11.3 Hz), 4.56 (dd, 2H, J=12.1, 22.8 Hz), 5.23 (d, 1H, J=11.0 Hz), 5.74 (d, 1H, J=17.6 Hz), 6.70 (dd, 1H, J=11.0, 17.6 Hz), 7.30 (d, 1H, J=8.3 Hz), 7.38 (d, 1H, J=8.3 Hz) $^{13}$C-NMR (CDCl$_3$) δ=40.2, 50.7, 70.7, 72.9, 113.8, 126.2, 127.9, 136.4, 137.0, 137.4

Referential Example 2

Synthesis of a Monomer Containing a Hydroxyalkyl Group Having an Oxygen Atom and a Polymerizable Double Bond

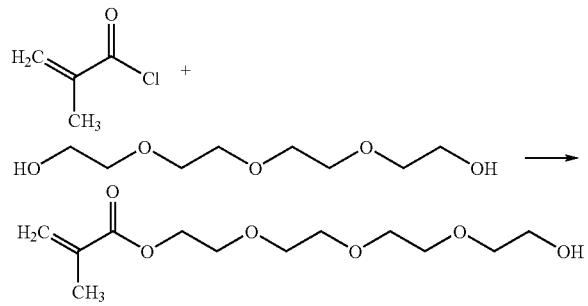

To 200 ml of methylene chloride, 7.0 ml of triethylamine and 9.71 g of tetraethylene glycol were added, and then they were cooled to 0° C., and 4.9 ml of methacryloyl chloride was added thereto. After the reaction mixture was reacted while stirring at room temperature for 12 hours, a solvent was distilled off under reduced pressure, and by adding diethyl ether to the residue, a hydrochloric acid salt of triethylamine was separated by filtration. The filtrate was condensed again under reduced pressure, and after methylene chloride was added to the residue and they were washed with water and saturated salt water, it was dried with sodium sulfate anhydride, followed by drying the solution, filtration and condensation under reduced pressure to obtain 10.3 g of a product (yield: 78%). According to the measurement results by $^1$H-NMR, it was affirmed that said product is tetraethylene glycol monomethacryloyl ester.

Referential Example 3

Synthesis of a Monomer Containing a Hydroxyalkyl Group Having an Oxygen Atom and a Polymerizable Double Bond (1) Synthesis of 3-hydroxy-2-phenylpropene

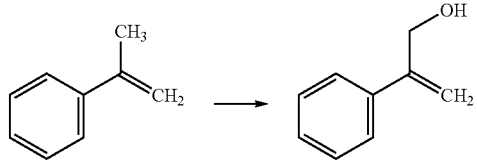

A 12.5 ml of decane solution of 5 to 6 mol/L of per-tert-butylalcohol is diluted with 50 ml of methylene chloride, then 111 mg of selenium dioxide and 90.1 mg of an acetic acid were added thereto to react while stirring at room temperature for 30 min. Then, 6.5 ml of 2-phenylpropene was added to the reaction solution to react while stirring for 72 hours, followed by condensation under reduced pressure, and purification by silica gel column chromatography to obtain 3.98 g of 3-hydroxy-2-phenylpropene (yield: 59%). Measurement results by $^1$H-NMR and $^{13}$C-NMR of 3-hydroxy-2-phenylpropene obtained are shown below.

$^1$H-NMR (CDCl$_3$) δ=1.27 (s, 1H), 4.55 (s, 2H), 5.36(s, 1H), 5.48 (s, 1H), 7.28-7.40 (m, 3H), 7.42-7.50 (m, 2H)

$^{13}$C-NMR (CDCl$_3$) δ=65.0, 112.6, 126.0, 127.9, 128.5, 138.4, 147.2

(2) Synthesis of 3-chloro-2-phenylpropene

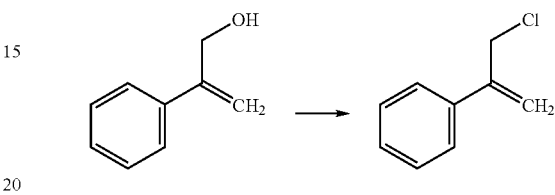

To 3.94 g of 3-hydroxy-2-phenylpropene obtained, a 10 ml of dimethylformamide solution containing 3.84 g of s-collidine and 1.245 g of lithium chloride was added, and they were cooled to 0° C. To a suspension obtained, 2.45 ml of methanesulfonyl chloride was added in drop-wise. After heating the reaction solution to room temperature over 8 hours, it was diluted with diethyl ether and the reaction was terminated by adding water. After separating an organic layer of the solution, a water layer was extracted twice with diethyl ether, and then it was combined with the organic layer separated, followed by washing with water and saturated salt water, and drying with sodium sulfate anhydride. After drying, this was filtrated and condensed under reduced pressure, and purified by silica gel column chromatography to obtain 3.53 g of 3-chloro-2-phenylpropene (yield: 79%). Measurement results by $^1$H-NMR and $^{13}$C-NMR of 3-chloro-2-phenylpropene obtained are shown below.

$^1$H-NMR (CDCl$_3$) δ=4.50 (s, 2H), 5.49(s, 1H), 5.60 (s, 1H), 7.30-7.60 (m, 5H)

$^{13}$C-NMR (CDCl$_3$) δ=46.5, 116.7, 126.1, 128.2, 128.5, 137.6, 143.9

(3) Synthesis of tetraethylene glycol mono-2-phenyl-2-propenyl ether

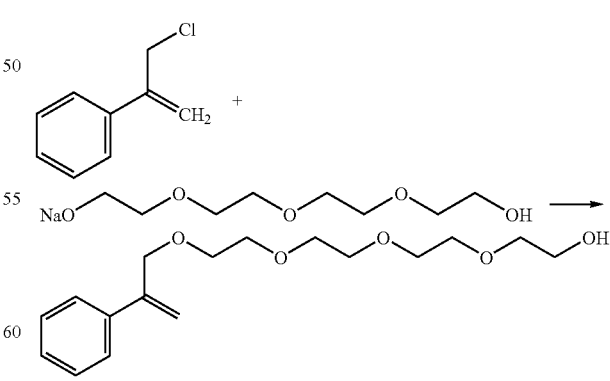

After 1.82 g of sodium hydride (purity: 60%) is washed with petroleum ether, it was dried under reduced pressure, followed by the addition of 70 ml of tetrahydrofuran thereto and cooling in an ice bath. Then, a solution dissolving 8.81 g of tetraethylene glycol was added to 10 ml of tetrahydrofuran in the system while stirring. After the reaction solution was reacted while stirring at room temperature for one hour, a solution dissolving 3.46 g of 3-chloro-2-phenylpropene obtained above in 10 ml of tetrahydrofuran was added in the system while stirring, and further they were reacted while stirring for 12 hours. After completing the reaction, the reaction solution was ice-cooled, and was diluted with diethyl ether and then the reaction was terminated by adding a saturated aqueous solution of ammonium chloride. After separating an organic layer of the reaction solution, a water layer was extracted with diethyl ether and it was combined with the organic layer separated. And the solution obtained was washed with a saturated aqueous solution of sodium bicarbonate and saturated salt water, and dried with sodium sulfate anhydride. After drying, this was filtrated and then condensed under reduced pressure, and purified by silica gel column chromatography to obtain 4.52 g of tetraethylene glycol mono-2-phenyl-2-propenyl ether (yield: 64%). Measurement results by $^1$H-NMR and $^{13}$C-NMR of tetraethylene glycol mono-2-phenyl-2-propenyl ether obtained are shown below.

$^1$H-NMR (CDCl$_3$) δ=2.72 (s, 1H), 3.58-3.74 (m, 16H), 4.42 (s, 2H), 5.34 (d, 1H, J=1.2 Hz), 5.53 (d, 1H, J=0.5 Hz), 7.25-7.36 (m, 3H), 7.44-7.52 (m, 2H)

$^{13}$C-NMR (CDCl$_3$) δ=61.7, 69.2, 70.3, 70.53, 70.58, 72.4, 73.1, 114.4, 126.1, 127.7, 128.3, 138.7, 144.0

Referential Example 4

Synthesis of a straight Chain Polymer Compound-1

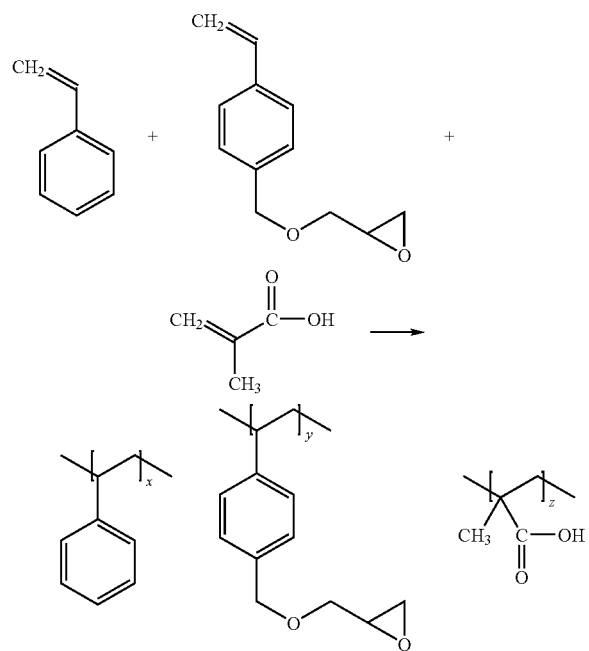

To 50 ml of toluene, 37.4 g of styrene, 3.8 g of 4-vinylbenzyl glycidyl ether obtained in Referential Example 1, 1.7 g of a methacrylic acid and 1 g of 2,2'-azobis(2,4-methylvaleronitrile) were added, and they were reacted by heating under refluxing at 70 to 80° C. for 8 hours. After completing the reaction, the reaction solution was cooled to room temperature, then dropped to 500 ml of ice-cooled hexane to solidify a polymer. The polymer solidified was filtered off, followed by dissolving in 50 ml of THF, and pouring 500 ml of hexane to re-precipitate. This operation was repeated, followed by drying under reduced pressure to obtain 11.8 g of a polymer (yield: 65%). According to the measurement results by $^1$H-NMR, ratio (X:Y:Z) of each monomer unit of the polymer obtained (styrene/4-vinylbenzyl glycidyl ether/methacrylic acid) was found to be 61:28:11. Weight average molecular weight M$_w$ of the polymer obtained was 19,504.

Referential Example 5

Synthesis of a Straight Chain Polymer Compound-2

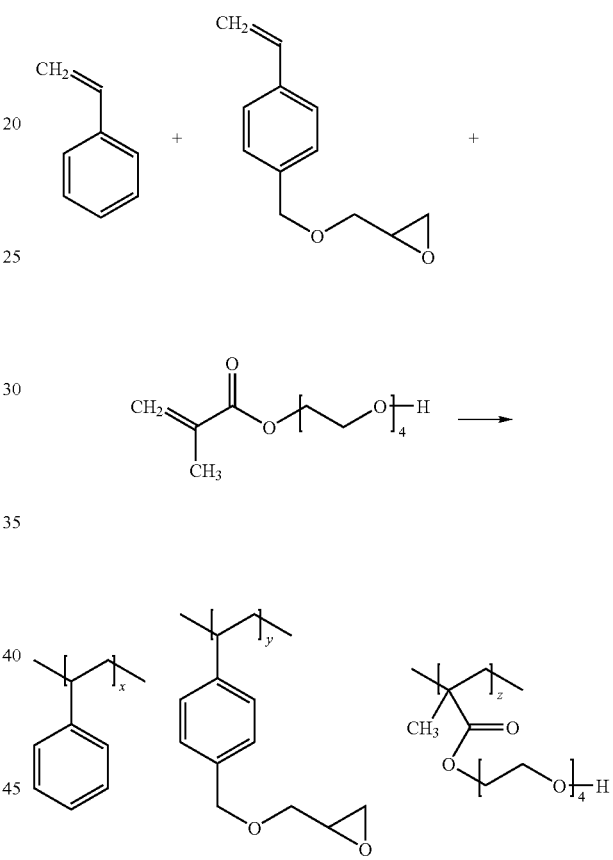

To 100 ml of chloroform, 23.3 g of styrene, 5.33 g of 4-vinylbenzyl glycidyl ether obtained in Referential Example 1, 7.74 g of tetraethylene glycol monomethacryloyl ester obtained in Referential Example 2, and 328.4 mg of 2,2'-azobisisobutyronitrile were added, and they were reacted by heating under refluxing at 80° C. for 48 hours. After completing the reaction, the reaction solution was cooled to room temperature, then dropped into 500 ml of ice-cooled methanol to solidify a polymer. The polymer solidified was filtered off, washed with methanol, and then dried under reduced pressure to obtain 23.03 g of a polymer (yield: 65%). According to the measurement results by $^1$H-NMR, ratio (X:Y:Z) of each monomer unit of the polymer obtained (styrene/4-vinylbenzyl glycidyl ether/tetraethylene glycol monomethacryloyl ester) was found to be 82:10:8. Weight average molecular weight M$_w$ of the polymer obtained was 22,087, number average molecular weight M$_n$ thereof was 12,473 and M$_w$/M$_n$ was 1.771.

Referential Example 6

Synthesis of a Straight Chain Polymer Compound-3

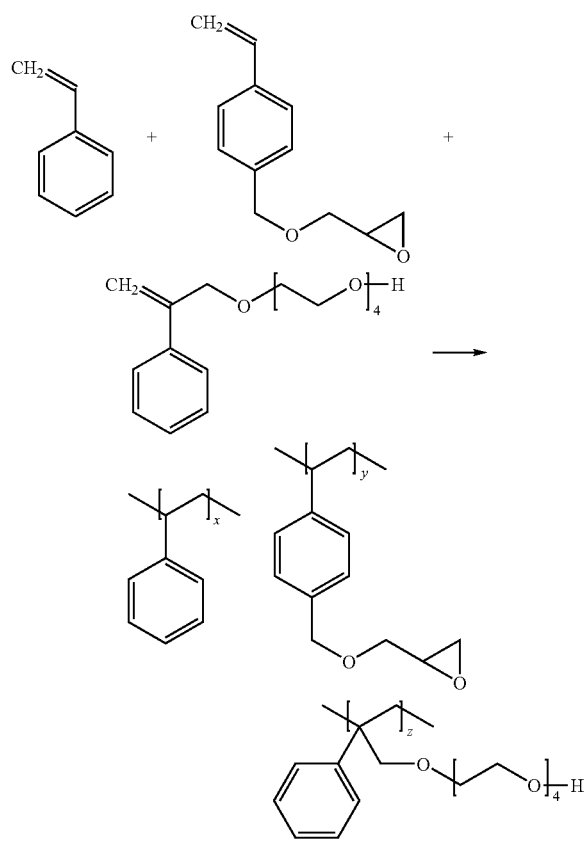

To 100 ml of chloroform, 23.3 g of styrene, 5.33 g of 4-vinylbenzyl glycidyl ether obtained in Referential Example 1, 9.08 g of tetraethylene glycol mono-2-phenyl-2-propenyl ether obtained in Referential Example 3, and 328.4 mg of 2,2'-azobisisobutyronitrile were added, and they were reacted by heating under refluxing at 80° C. for 48 hours. After completing the reaction, the reaction solution was cooled to room temperature, then dropped into 500 ml of ice-cooled methanol to solidify a polymer. The polymer solidified was filtered off, washed with methanol, and dried under reduced pressure to obtain 23.0 g of a polymer (yield: 68%). According to the measurement results by $^1$H-NMR, ratio (X:Y:Z) of each monomer unit of the polymer obtained (styrene/4-vinylbenzyl glycidyl ether/tetraethylene glycol mono-2-phenyl-2-propenyl ether) was found to be 90:4:6. Weight average molecular weight $M_w$ of the polymer obtained was 69,985, number average molecular weight $M_n$ thereof was 12,098 and $M_w/M_n$ was 5.785.

Example 1

Synthesis of a Catalyst Composition of the Present Invention (Carried on an MSV Polymer)

Into 20 ml of tetrahydrofuran, 1.0 g of a straight chain polymer compound obtained in Referential Example 4 was dissolved, and 200 mg of tetrakis (triphenylphosphine) palladium was added thereto, and they were reacted while stirring at room temperature for 24 hours. After completing the reaction, hexane, which is a poor solvent of the reaction solution, was added thereto to solidify a polymer, and they were left to stand for 12 hours. After decantation of a hexane layer, the polymer was dried under reduced pressure. After the polymer obtained was pulverized, it was agitated at 120° C. for 2 hours in non-solvent condition, and the polymer was cooled to room temperature. Then, tetrahydrofuran was added thereto and they were agitated, followed by filtering off, washing with tetrahydrofuran and drying under reduced pressure to obtain 750 mg of a catalyst composition of the present invention.

From the filtrate, whole amount of triphenylphosphine could be recovered corresponding to that of tetrakis(triphenylphosphine) palladium used. Introduction ratio of palladium metal on a polymer carrier was 93%, and palladium metal contained in 1 g of a catalyst composition of the present invention was 0.215 mmol.

In this connection, introduction ratio of palladium metal was determined by measuring residual palladium metal in filtrate using a fluorescent X-ray spectrometer, and by comparing with amount of metal used in a reaction (the same hereinafter).

Example 2

Synthesis of a Catalyst Composition of the Present Invention

Into 20 ml of tetrahydrofuran, 1.0 g of a straight chain polymer compound obtained in Referential Example 6 was dissolved, and 100 mg of tetrakis (triphenylphosphine) palladium was added thereto, and they were reacted while stirring at room temperature for 24 hours. After completing the reaction, hexane, which is a poor solvent of the reaction solution, was added thereto to solidify a polymer, and they were left to stand for 12 hours. After decantation of a hexane layer, the polymer was dried under reduced pressure. After the polymer obtained was pulverized, it was agitated at 120° C. for 2 hours in non-solvent condition, and cooled to room temperature. Then, tetrahydrofuran was added thereto and they were agitated, followed by filtering off, washing with tetrahydrofuran and drying under reduced pressure to obtain 750 mg of a catalyst composition of the present invention. From the filtrate, whole amount of triphenylphosphine could be recovered corresponding to that of tetrakis(triphenylphosphine) palladium used. And introduction ratio of palladium metal on a polymer carrier was 97%, and palladium metal contained in 1 g of a catalyst composition of the present invention was 0.108 mmol.

Example 3

Synthesis of a Catalyst Composition of the Present Invention

The same procedure as Example 2 was conducted except that a straight chain polymer compound obtained in Referential Example 5 was used as a polymer carrier instead of a straight chain polymer compound obtained in Referential Example 6, and 792 mg of a catalyst composition of the present invention was obtained. From the filtrate, whole amount of triphenylphosphine was recovered corresponding to that of tetrakis(triphenylphosphine) palladium used. And introduction ratio of palladium metal on a polymer carrier was 97%, and palladium metal contained in 1 g of a catalyst composition of the present invention was 0.108 mmol.

Experimental Example 1

Hydrogenation Reaction of an Olefin-1

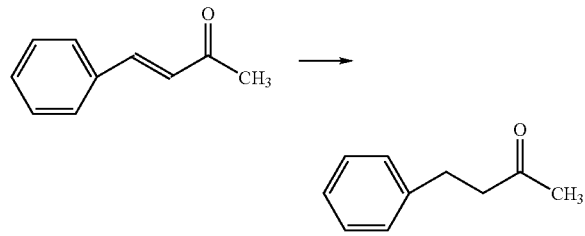

To 5 ml of tetrahydrofuran, 115 mg of a catalyst composition of the present invention (palladium metal content: 0.025 mmol) obtained in Example 1 and 73.0 mg of benzalacetone were added, and they were reacted while stirring under hydrogen atmosphere at room temperature for one hour. After completing the reaction, hexane was added to the reaction solution and they were agitated. When the reaction solution became transparent, the catalyst composition of the present invention used was filtrated. After a filtrate was condensed, it was purified by silica gel thin-layer chromatography to obtain 50.3 mg of 4-phenyl-2-butanone (yield: 68%). By measurement of the filtrate before purifying with a fluorescent X-ray spectrometer, it was affirmed that palladium leakage was not observed from a catalyst composition of the present invention.

And a catalyst composition of the present invention filtered off was washed with tetrahydrofuran, and then recovered by drying under reduced pressure.

It was proved by the measurement results using $^1$H-NMR and $^{13}$C-NMR that a product obtained is 4-phenyl-2-butanone.

Experimental Example 2

Hydrogenation Reaction of an Olefin-2

To 5 ml of tetrahydrofuran, 231 mg of a catalyst composition of the present invention (palladium metal content: 0.025 mmol) obtained in Example 2 and 73.0 mg of benzalacetone were added, and they were reacted while stirring under hydrogen atmosphere at room temperature for one hour. After completing the reaction, hexane was added to the reaction solution, followed by stirring and filtering a catalyst composition of the present invention used, when the reaction solution became transparent. After the filtrate was condensed, it was purified by silica gel thin-layer chromatography to obtain 60.0 mg of 4-phenyl-2-butanone (yield: 81%). By measurement of the filtrate before purifying with fluorescent X-ray measurement, it was affirmed that palladium leakage was not observed from a catalyst composition of the present invention.

A catalyst composition of the present invention filtered off was washed with tetrahydrofuran, and then recovered by drying under reduced pressure.

It was confirmed by the measurement result using $^1$H-NMR and $^{13}$C-NMR that the product obtained is 4-phenyl-2-butanone.

The same operations as described above were repeated 4 times using the recovered catalyst composition of the present invention again as a catalyst. Repeated use times of the catalyst and yield of 4-phenyl-2-butanone obtained in each reaction are shown in Table 1.

Experimental Example 3

Hydrogenation Reaction of an Olefin-3

The same reaction as in Experimental Example 1 was conducted except that a catalyst composition of the present invention obtained in Example 3 was used instead of the catalyst composition of the present invention obtained in Example 2. Yields of 4-phenyl-2-butanone obtained are also represented in Table 1.

Comparative Example 1

Hydrogenation Reaction of an Olefin

The same reaction as in Experimental Example 1 was conducted except that a palladium carbon (Pd content: 5%) was used instead of the catalyst composition of the present invention. Yield of 4-phenyl-2-butanone obtained is also shown in Table 1.

TABLE 1

|  | 1st time | 2nd time | 3rd time | 4th time | 5th time |
|---|---|---|---|---|---|
| Experimental Example 1 | 81% | — | — | — | — |
| Experimental Example 2 | 93% | 80% | 88% | 82% | 87% |
| Experimental Example 3 | 85% | 80% | 87% | 91% | 90% |
| Comparative Example 1 | 91% | — | — | — | — |

In this Table, "-" indicates "not experimented." (the same in Tables hereinafter).

As clear from Table 1, it is proved that a catalyst composition of the present invention has equivalent activity to that of a conventionally used catalyst, and even by many times repeated use little decrease in activity was observed.

Example 4

A substitution Reaction at an Allyl Position-1

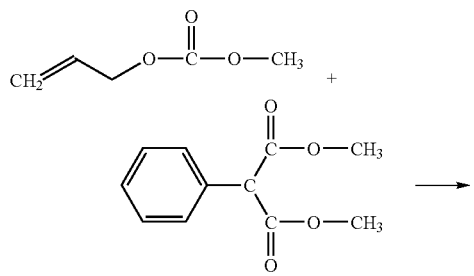

-continued

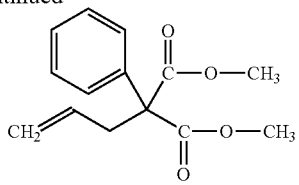

In the presence of 115 mg of the catalyst composition of the present invention (palladium metal content: 0.025 mmol) obtained in Example 1 and 26.3 mg of triphenylphosphine, 63.9 mg of allyl methyl carbonate and 104.1 mg of dimethyl phenylmalonate were added to 5 ml of tetrahydrofuran, and they were reacted by heating under dry distillation for 12 hours. After completing the reaction, hexane was added to the reaction solution and stirred. When the reaction solution became transparent, a catalyst composition of the present invention was filtered off. After a filtrate was condensed, it was purified by silica gel thin-layer chromatography to obtain 67.1 mg of dimethyl allylphenylmalonate (yield: 54%). By measurement of the filtrate before purifying with a fluorescent X-ray spectrometer, no palladium leakage was observed from a catalyst composition of the present invention.

A catalyst composition of the present invention filtered off was washed with tetrahydrofuran, and then recovered by drying under reduced pressure.

The same operations as described above were repeated twice using the recovered catalyst composition of the present invention again as a catalyst. Repeated use times of the catalyst and yield of dimethyl allylphenylmalonate obtained in each reaction are shown in Table 2.

Example 5

A Substitution Reaction at an Allyl Position-2

In the presence of 231 mg of the catalyst composition of the present invention (palladium metal content: 0.025 mmol) obtained in Example 2 and 26.3 mg of triphenylphosphine, 63.9 mg of allyl methyl carbonate and 104.1 mg of dimethyl phenylmalonate were added to 5 ml of tetrahydrofuran, and they were reacted by heating and dry distillation for 12 hours. After completing the reaction, hexane was added to the reaction solution and stirred. When the reaction solution became transparent, a catalyst composition of the present invention was filtered off. After a filtrate was condensed, it was purified by silica gel thin-layer chromatography to obtain 109.3 mg of dimethyl allylphenylmalonate (yield: 88%). By measurement of the filtrate before purifying with a fluorescent X-ray spectrometer, no palladium leakage was observed from a catalyst composition of the present invention.

A catalyst composition of the present invention filtered off was washed with tetrahydrofuran, and then recovered by drying under reduced pressure.

The same operations as described above were repeated 4 times using the recovered catalyst composition of the present invention again as a catalyst. A catalyst composition of the present invention did not show palladium leakage even by the above-described repeated use of 5 times in total.

Repeated use times of the catalyst and yield of dimethyl allylphenylmalonate obtained in each reaction are also shown in Table 2.

Example 6

A Substitution Reaction at an Allyl Position-3

The same reaction as in Example 5 was conducted except that a catalyst composition of the present invention obtained in Example 3 was used instead of the catalyst composition of the present invention obtained in Example 2. Repeated use number of the catalyst and yield of dimethyl allylphenylmalonate obtained in each reaction are also shown in Table 2.

TABLE 2

|  | 1st time | 2nd time | 3rd time | 4th time | 5th time |
| --- | --- | --- | --- | --- | --- |
| Example 4 | 54% | 82% | 97% | — | — |
| Example 5 | Quant | 85% | 89% | 95% | 82% |
| Example 6 | 95% | 100% | 94% | 94% | 71% |

As clear from Table 2, it is proved that a catalyst composition of the present invention showed little decrease in activity even by many times of repeated use. Further, it is proved from Example 5 that even by many times of repeated use, a catalyst composition of the present invention does not exhibit metal leakage from a polymer carrier.

Example 7

A Substitution Reaction at an Allyl Position-4

The same substitution reaction at an allyl position was conducted as in Example 6, except that a reaction period was 2 hours. And by recovering the catalyst used, the same reactions were repeated 5 times. Repeated use number of the catalyst and yield of dimethyl allylphenylmalonate obtained in each reaction are shown in Table 3. In all of the reactions, metal leakage from a catalyst composition of the present invention was not observed.

TABLE 3

|  | 1st time | 2nd time | 3rd time | 4th time | 5th time |
| --- | --- | --- | --- | --- | --- |
| Example 7 | 88% | 94% | 98% | 87% | 98% |

As clear from Example 7, it is proved that a catalyst composition of the present invention obtained in Example 3 has favorable activity even though a reaction period is significantly shortened.

Examples 8 to 12

A Substitution Reaction at an Allyl Position

The same substitution reaction at an allyl position was conducted as in Example 7, except that 0.55 mmol of allyl carbonate as described in Table 4 below and 0.50 mmol of a nucleophilic agent as described in Table 4 were used. Compounds obtained in each reaction and yields thereof are also shown in Table 4.

TABLE 4

| | Allyl carbonate (Amount used) | Nucleophilic agent (Amount used) | Product (Amount of yield) | | Yield |
|---|---|---|---|---|---|
| Ex. 8 | ethyl 2-methylallyl carbonate (79.3 mg) | dimethyl phenyl malonate (104.1 mg) | dimethyl 2-methylallylphenylmalonate (123.3 mg) | | 94% |
| Ex. 9 | allyl methyl carbonate (63.9 mg) | | 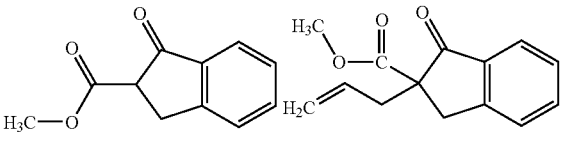 (95.1 mg) | 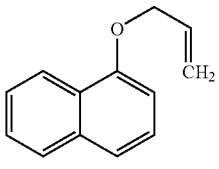 (108.2 mg) | 94% |
| Ex. 10 | allyl methyl carbonate (63.9 mg) | 1-naphthol (72.1 mg) | 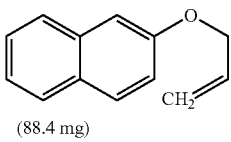 (92.1 mg) | | Quant |
| Ex. 11 | allyl methyl carbonate (63.9 mg) | 2-naphthol (72.1 mg) | (88.4 mg) | | 96% |
| Ex. 12 | allyl methyl carbonate (63.9 mg) | p-nitrophenol (69.6 mg) | 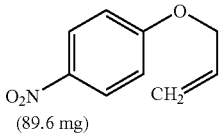 (89.6 mg) | | 100% |

Generally, it is known that when a nucleophilic agent containing oxygen, such as phenol having an electron accepting group such as a nitro group, and the like, is used, reactivity in a substitution reaction at an allyl position is remarkably decreased. However, As clear from Example 12 in Table 4, it is proved that when a catalyst composition of the present invention is used, even when a nucleophilic agent containing oxygen with an electron accepting group, is used, a reaction proceeds extremely effectively. From this, it can be understood that a catalyst composition of the present invention has high catalytic activity as compared with a conventional catalyst.

Example 13

An Oxidation Reaction of an Alcohol

To 5 ml of acetonitrile, 0.025 mmol of the catalyst composition of the present invention obtained in Example 3, 67.1 mg of cinnamyl alcohol and 63.9 mg of allyl methyl carbonate were added, and they were reacted while stirring at 80° C. for 2 hours. After completing the reaction, the catalyst composition of the present invention was filtered off. After a filtrate was condensed, it was purified by silica gel thin-layer chromatography to obtain 45.4 mg of cinnamaldehyde (yield: 69%). By measurement of the filtrate before purifying with fluorescent X-ray measurement, palladium leakage was not observed from a catalyst composition of the present invention.

A catalyst composition of the present invention filtered off was washed with tetrahydrofuran, and then recovered by drying under reduced pressure.

As clear from Example 13, it is proved that a phosphine ligand does not exist in a reaction system, since by using a catalyst composition of the present invention, cinnamyl alcohol is oxidized without inducing a substitution reaction at an allyl position. That is, it is proved that in a catalyst composition of the present invention, a triphenylphosphine ligand used in synthesis thereof is not contained at all.

INDUSTRIAL APPLICABILITY

A catalyst composition wherein a 0 valence metal catalyst physically carried on a crosslinked organic polymer compound, can be obtained by homogenizing a straight chain organic polymer compound having a crosslinkable functional group and a 0 valence metal catalyst coordinated with a ligand, in a solvent which dissolves these, followed by deposition of the composition produced, and subjecting a crosslinkable functional group in said deposited material to a crosslinking reaction for condensation reacting. Furthermore, the catalyst composition thus obtained can be safely and easily handled without danger of spontaneous ignition, and the like, and is extremely useful as a catalyst for various chemical reactions, and further, activity thereof is not lowered by repeated use, and a metal catalyst does not leak at all from a polymer carrier compound.

What is claimed is:

1. A catalyst composition comprising a crosslinked organic polymer compound and Pd(0) having no ligand, wherein said Pd(0) is physically carried on said crosslinked organic polymer compound, prepared by homogenizing a straight chain organic polymer compound having a crosslinkable functional group, and a palladium catalyst in a solvent dissolving said straight chain organic polymer compound;

then depositing the composition formed; and subjecting a crosslinkable functional group in said deposited composition to a crosslinking reaction, and wherein said straight chain organic polymer compound is obtained by polymerizing 1) a monomer having a crosslinkable functional group and a polymerizable double bond represented by:

(1) a glycidyl compound having an epoxy group as a crosslinkable functional group, selected from the group consisting of a glycidyl ether and a glycidyl ester represented by the following general formulas [1] and [2], respectively,

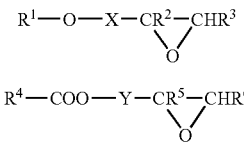

wherein $R^2$, $R^3$, $R^5$ and $R^6$ each independently represents a hydrogen atom or an alkyl group having 1 to 6 carbon atoms; X and Z each independently represents an alkylene group having 1 to 6 carbon atoms; $R^2$ may form a ring of 3 to 6 members together with carbon atoms of $R^3$ or X, and $R^5$ may form a ring of 3 to 6 members together with carbon atoms of $R^6$ or Z; and $R^1$ and $R^4$ each independently is a group represented by the following general formula [3]:

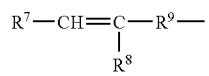

wherein $R^7$ and $R^8$ each independently represents a hydrogen atom or an alkyl group having 1 to 6 carbon atoms; $R^9$ represents a direct-linkage, an alkylene group having 1 to 6 carbon atoms, an arylene group having 6 to 9 carbon atoms, an arylalkylene group having 7 to 12 carbon atoms or an arylenealkylene group having 7 to 15 carbon atoms, wherein the aromatic ring in the arylene or arylenealkylene group may have an alkyl group having 1 to 4 carbon atoms, an alkoxy group having 1 to 4 carbon atoms and/or a halogen atom, as a substituent;

(2) a monomer having a carboxyl group as a crosslinkable functional group, represented by the following general formula [4]:

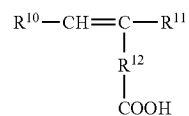

wherein $R^{10}$ represents a hydrogen atom or an alkyl group having 1 to 6 carbon atoms; $R^{11}$ represents a hydrogen atom, an alkyl group having 1 to 6 carbon atoms, an aryl group having 6 to 10 carbon atoms or an aralkyl group having 7 to 12 carbon atoms, wherein the aromatic ring in the aryl group or aralkyl group may have an alkyl group having 1 to 4 carbon atoms, an alkoxy group having 1 to 4 carbon atoms and/or a halogen atom as a substituent; and $R^{12}$ represents a direct-linkage, an alkylene group having 1 to 6 carbon atoms, an arylene group having 6 to 9 carbon atoms, an arylalkylene group having 7 to 12 carbon atoms or an arylenealkylene group having 7 to 15 carbon atoms; or (3) a monomer having a hydroxyl group as a crosslinkable functional group, represented by the following general formula [5]:

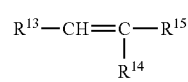

wherein $R^{13}$ represents a hydrogen atom or an alkyl group having 1 to 20 carbon atoms; $R^{14}$ represents a hydroxyalkyl group that may have a carbonyl group and/or an oxygen atom; $R^{15}$ represents a hydrogen atom, an alkyl group having 1 to 6 carbon atoms, an aryl group having 6 to 10 carbon atoms or an aralkyl group having 7 to 12 carbon atoms; and an aromatic ring in the above aryl group or aralkyl group may have an alkyl group having 1 to 4 carbon atoms, an alkoxy group having 1 to 4 carbon atoms and/or a halogen atom, as a substituent, and optionally 2) a monomer having a polymerizable double bond is represented by the general formula [6]:

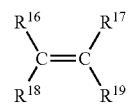

wherein $R^{16}$ and $R^{17}$ each independently represent a hydrogen atom or an alkyl group having 1 to 6 carbon atoms; $R^{19}$ represents a hydrogen atom, a halogen atom or an alkyl group having 1 to 6 carbon atoms; $R^{18}$ represents a carboxyl group, a hydroxyl group, an acyloxy group having 2 to 6 carbon atoms, an arylacyloxy group having 7 to 15 carbon atoms, an alkoxycarbonyl group having 2 to 6 carbon atoms, an alkyl group having 1 to 6 carbon atoms, an aryl group having 6 to 10 carbon atoms and an aralkyl group having 7 to 12 carbon atoms; an aromatic ring in the above arylacyloxy group, aryl group and aralkyl group, may have further an alkyl group having 1 to 4 carbon atoms, an alkoxy group having 1 to 4 carbon atoms or a halogen atom, as a substituent, and wherein all of monomers having a crosslinkable functional group and a polymerizable double bond represented by the general formulas [1], [2], [4] and [5], and of monomers having a polymerizable double bond represented by the general formula [6], have an aromatic ring.

2. The composition according to claim 1, wherein the crosslinked organic polymer compound is:

a crosslinked product of a copolymer obtained by copolymerizing 1) at least one monomer having a crosslinkable functional group and a polymerizable double bond selected from the group consisting of (1) said glycidyl compound having an epoxy group, (2) said monomer having a carboxyl group, and (3) said monomer having a hydroxyalkyl group, and 2) at least one monomer having a polymerizable double bond which is represented by the general formula [6].

3. The composition according to claim 2, wherein the crosslinked organic polymer compound is a crosslinked product of a copolymer obtained by copolymerizing:

1) two monomers having a crosslinkable functional group and a polymerizable double bond and 2) one monomer having a polymerizable double bond.

4. The composition according to claim 2, wherein ratio of a monomer unit derived from a monomer having a crosslinkable functional group and a polymerizable double bond is 0.1 to 100% based on all monomer units in the whole copolymer before crosslinking of the crosslinked organic polymer compound.

5. The composition according to claim 3, wherein:

one monomer having a crosslinkable functional group and a polymerizable double bond is a glycidyl ether represented by the general formula [1]; and the other monomer having a crosslinkable functional group is a monomer represented by the general formula [4] containing a carboxyl group, as a crosslinkable functional group, or a monomer represented by the general formula [5] containing a hydroxyl group as a crosslinkable functional group.

6. The composition according to claim 2, wherein in (3) said monomer having a hydroxyl group as a crosslinkable functional group, represented by the general formula [5], $R^{14}$ is a straight chain hydroxyalkyl group having 1 to 50 carbon numbers, which may contain an oxygen atom.

7. The composition according to claim 2, wherein the crosslinked organic polymer compound has a crosslinked portion between an alkylene chain derived from a polymerizable double bond, and another alkylene chain derived from a polymerizable double bond, and the number of atoms in the shortest chain of said crosslinked portion is 1 to 400.

8. A method for producing the composition according to claim 1, comprising the steps of:

homogenizing a straight chain organic polymer compound having a crosslinkable functional group, and a palladium catalyst in a solvent which dissolves said straight chain organic polymer compound;

depositing the composition produced; and subjecting a crosslinkable functional group in said deposited composition to a crosslinking reaction.

9. The method for production according to claim 8, wherein the palladium catalyst is a complex with triphenylphosphine, tri-t-butylphosphine, triethylphosphine, or trimethylphosphine.

10. A method for performing an oxidization reaction of an alcohol, comprising the steps of:

reacting the composition according to claim 1 with a primary alcohol to form a aldehype compound corresponding to the alcohol.

* * * * *